United States Patent
Bailey et al.

(12)

(10) Patent No.: US 6,441,189 B1
(45) Date of Patent: Aug. 27, 2002

(54) PROCESS FOR THE PREPARATION OF MATRIX METALLOPROTEINASE INHIBITORS

(75) Inventors: Anne E. Bailey, Beach Park; David R. Hill, Gurnee; Chi-nung W. Hsiao, Libertyville; Ravi Kurukulasuriya, Gurnee; Steve Wittenberger, Mundelein; Todd McDermott, Oak Park; Maureen A. McLaughlin, Gurnee, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/020,326

(22) Filed: Dec. 13, 2001

Related U.S. Application Data

(63) Continuation of application No. 09/821,887, filed on Mar. 30, 2001, now abandoned.
(60) Provisional application No. 60/194,069, filed on Mar. 31, 2000.

(51) Int. Cl.⁷ .............................................. C07D 263/06
(52) U.S. Cl. ...................................................... 548/232
(58) Field of Search ........................................ 548/232

(56) References Cited

U.S. PATENT DOCUMENTS

| | | |
|---|---|---|
| 4,139,538 A | 2/1979 | Kollensperger et al. |
| 5,684,152 A | 11/1997 | Ponipipom et al. |

FOREIGN PATENT DOCUMENTS

| | | |
|---|---|---|
| EP | 0327307 | 9/1989 |
| FR | 2545488 | 11/1984 |
| WO | 9906361 | 11/1999 |

OTHER PUBLICATIONS

Sibi, Mukund P.; "A New Electrophilic Alaninol Synthon. A General Route to Oxazolidinones of D or (R)–2–Amino Alcohols from L–Serine", Journal of Chem. Soc. Perkin Trans.; vol. 13. No. 1, pp. 1675–1678, (1994).

Allin, S. et al., "The preparation and first application of a polymer–supported Evans oxazolidinone," Tetrahedron Letters 37(44):8023–8026 (1996).

Saijo, S. et al., "Heterocyclic prostaglandins. VI. Synthesis of 11–deoxy–8, 10–diazaprostaglandin E1 and its 10–mthyl derivative," Chemical & Pharmaceutical Bulletin 28(5):1459–1467 (1980).

Sibi, M. P. et al., "Investigation of a nucleophilic alanilol synthon derived from serine," Journal of the American Chemical Society 121(33):7509–7516 (1999).

*Primary Examiner*—Joseph K. McKane
*Assistant Examiner*—Kamal Saeed
(74) *Attorney, Agent, or Firm*—Gregory W. Steele

(57) ABSTRACT

The instant invention provides a process for the synthesis of matrix metalloproteinase inhibitors.

4 Claims, No Drawings

PROCESS FOR THE PREPARATION OF MATRIX METALLOPROTEINASE INHIBITORS

CROSS-REFERENCE TO RELATED APPLICATIONS

This application is a continuation of U.S. Ser. No. 09/821,887, filed Mar. 30, 2001, now abandoned, which claims the benefit of U.S. Provisional Application Ser. No. 60/194,069, filed Mar. 31, 2000.

TECHNICAL FIELD

This invention relates to a process for the preparation of matrix metalloproteinase inhibitors and to intermediates useful in the process.

BACKGROUND OF THE INVENTION

Matrix metalloproteinases are a class of extracellular enzymes such as collagenase, stromelysin, and gelatinase which are believed to be involved in tissue destruction which accompanies a number of diseases including arthritis and cancer. There is, therefore, a continuing need for compounds which are inhibitors of matrix matalloproteinase.

The instant invention discloses a synthesis of metalloproteinase inhibitors from ((4S)-2-oxo-1,3-oxazolidin-4-yl) methyl 4-methylbenzenesulfonate (Sibi, M. P., Rutherford, D., Sharma, R. *J Chem. Soc. Perkin Trans.* 1994, 13, 1, 1675). Although an efficient synthesis of this compound has been reported, racemization occurs during the sequence, causing a reduction in the enantiomeric excess of the final product. This invention discloses a method for the preparation of ((4S)-2-oxo-1,3-oxazolidin-4-yl)methyl 4-methylbenzenesulfonate which significantly reduces racemization.

SUMMARY OF THE INVENTION

In one embodiment of the instant invention is disclosed a process for preparing a compound of formula (3)

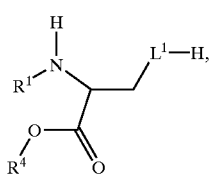

(3)

wherein $R^1$ is selected from the group consisting of hydrogen, an amino protecting group, and $-OR^2$;

$R^2$ is hydrogen or a hydroxy protecting group;

$L^1$ is $-O-$ or $-N(R^3)-$, wherein $R^3$ is hydrogen or an amino protecting group; and X is O or S, the process comprising:

(a) reacting a compound of formula (2)

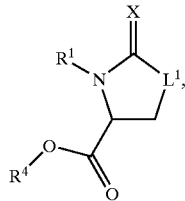

(2)

wherein $R^4$ is a carboxyl protecting group, with a reducing agent to provide a first reaction mixture; and (b) adjusting the pH of the first reaction mixture to about 2 to about 6; and (c) isolating the compound of formula (3).

In a preferred embodiment the compound of formula (3) is (4R)-4-(hydroxymethyl)-1,3-oxazolidin-2-one.

Another embodiment of the instant invention comprises reacting a compound of formula (1)

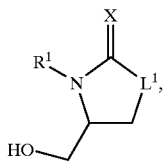

(1)

a base, and a reagent selected from the group consisting of phosgene, thiophosgene, triphosgene, carbonyldiimidazole, thiocarbonyldiimidazole, and a dialkyl carbonate.

Another embodiment of the instant invention comprises a process for preparing a compound of formula (5-a)

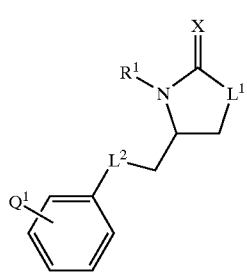

(5-a)

or a compound of formula (5-b)

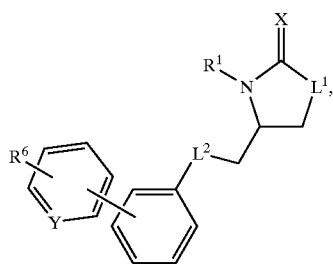

(5-b)

wherein $Q^1$ is selected from the group consisting of halide, methanesulfonate, and trifluoromethanesulfonate;

Y is nitrogen or C(H);

$R^6$ is selected from the group consisting of alkoxy, alkoxyalkyl, alkyl, aminosulfonyl, aminosulfonylalkyl, aryl, arylalkyl, cyano, cyanoalkyl, halo, haloalkyl, (heterocycle)oxy, (heterocycle)oxyalkyl, hydroxy, hydroxyalkyl, phenylalkoxy, phenylalkoxyalkyl phenoxy, phenoxyalkyl, perfluoroalkoxy, perfluoroalkoxyalkyl, perfluorothioalkoxy, perfluorothioalkoxyalkyl, sulfinyl, sulfinylalkylsulfonyl, sulfonylalkyl, thioalkoxy, and thioalkoxyalkyl; and $L^2$ is —O— or —S—, the process comprising:

(a) activating the hydroxyl of the compound of formula (3)

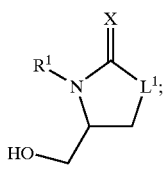
(3)

(b) reacting the product of step (a), a compound of formula (4)

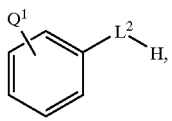
(4)

and base to provide the compound of formula (5-a)

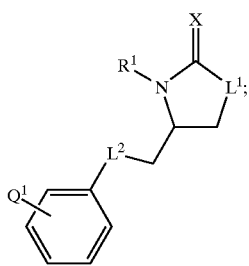
(5-a)

(c) optionally oxidizing the product of step (b); and
(d) optionally reacting the product of step (b) or step (c) and a compound of formula (6)

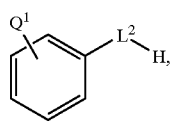
(6)

wherein
$Q^2$ is selected from the group consisting of trialkylstannanes, boronic acid, boronic esters, magnesium halides, zinc halides, and silyl(alkyl) cyclobutanes, and a coupling catalyst.

In a preferred embodiment the compound of formula (5-a) is
(4R)-4-((4-bromophenoxy)methyl)-1,3-oxazolidin-2-one and the compound of formula (5-b) is
(4R)-4-(((4'-(trifluoromethoxy)(1,1'-biphenyl)-4-yl)oxy) methyl)-1,3-oxazolidin-2-one.

Another embodiment of the instant invention comprises a process for preparing a compound of formula (5-c)

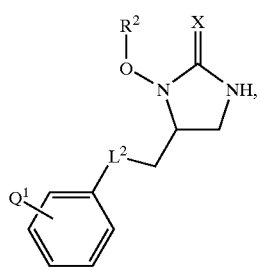
(5-c)

the process comprising:

(a) reacting a compound of formula (7)

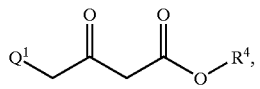
(7)

wherein
$R^4$ is alkyl, a compound of formula (4)

(4)

and base to provide a compound of formula (8)

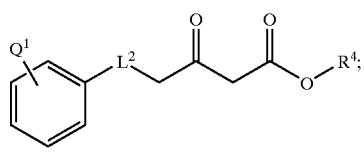
(8)

(b) optionally reacting the product from step (a) and an oxidant;

(c) reacting the product of step (a) or step (b), hydrogen, and a hydrogenation catalyst to provide a compound of formula (9)

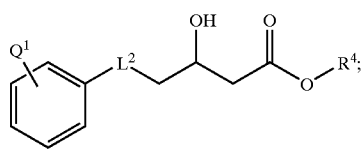
(9)

(d) reacting the product from step (c) and base to provide a compound of formula (10)

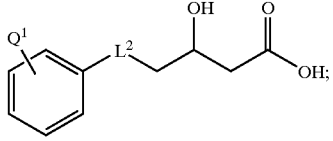
(10)

(e) reacting the product from step (d) and a compound of formula $H_2NOR^2$, or a salt thereof, wherein
  $R^2$ is a hydroxyl protecting group, under dehydrating conditions to provide a compound of formula (11)

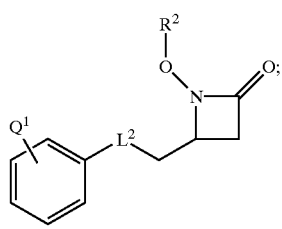
(11)

(f) reacting the product of step (e) under Mitsunobu conditions to provide a compound of formula (12)

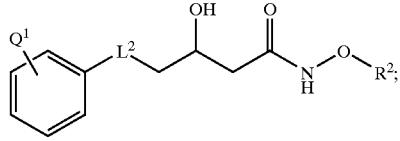
(12)

(g) reacting the product from step (f) and base to provide a compound of formula (13)

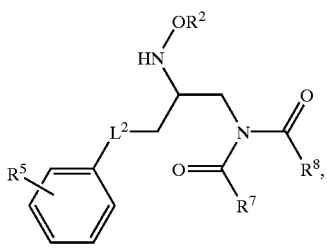
(13)

and (h) reacting the product from step (g) and azide under dehydrating conditions.

In a preferred embodiment the compound of formula (5-c) is
(5R)-1-(benzyloxy)-5-((4-bromophenoxy)methyl)-2-imidazolidinone.

Another embodiment of the instant invention comprises a process for preparing a compound of formula (15)

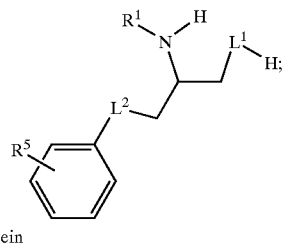
(15)

wherein

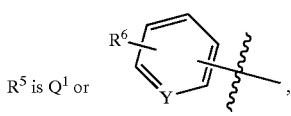

$R^5$ is $Q^1$ or the process comprising:

(a) reacting a compound of formula (5)

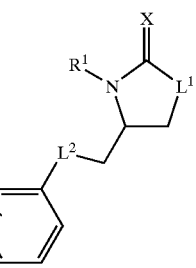
(5)

and base.

In a preferred embodiment the compound of formula (15) is selected from the group consisting of
(2S)-2-amino-3-((4'-(trifluoromethoxy)(1,1'-biphenyl)-4-yl)oxy)-1-propanol,
(2S)-2-amino-3-(4-bromophenoxy)-1-propanol, and
(2R)-2-((benzyloxy)amino)-3-(4-bromophenoxy)-1-propanamine.

Another embodiment of the instant invention comprises a process for preparing of a compound of formula (20), (20)

or a salt thereof, wherein $R^7$ and $R^8$, together with the atoms to which they are attached, form a heterocycle selected from the group consisting of 5,5-dimethyl-1,3-oxazolidine-2,4-dionyl; 1-methyl-2,4-imidazolidinedionyl; 1,5,5-trimethyl-2,4-imidazolidinedionyl; 2,4-imidazolidinedionyl; 5,5-dimethyl-2,4-imidazolidinedionyl; 1,2-dimethyl-1,2,4-triazolidine-3,5-dionyl; 4,4-dimethyl-2,6- piperidinedione; 8-azaspiro(4.5)decane-7,9-dionyl; 3a,6-dihydro-1H-benzo(de)isoquinoline-1,3(2H)-dionyl; 2,4(1H,3H)-quinazolinedionyl; 1-methyl-2,4(1H,3H)-pyrimidinedionyl; and 1,1-dioxo-1,2-benzisothiazol-3(2H)-onyl, the process comprising:

(a) reacting a compound of formula (15-a)

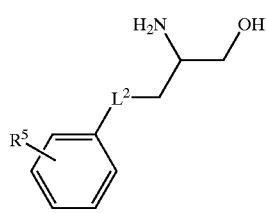

(15-a)

and a compound of formula R⁹—CHO, wherein R⁹ is optionally substituted aryl, to provide a compound of formula (16)

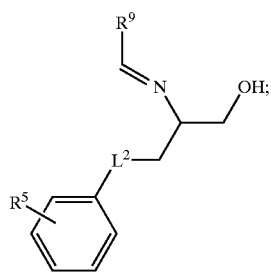

(16)

(b) reacting the product of step (a) and a compound of formula (17) under Mitsunobu conditions

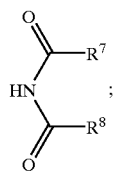

(17)

to provide a compound of formula (18)

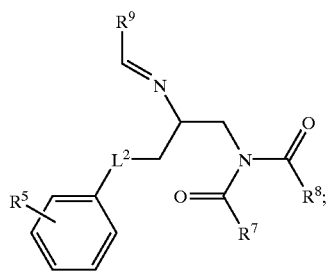

(18)

(c) reacting the product of step (b) and an oxaziridine forming agent to provide a compound of formula (19)

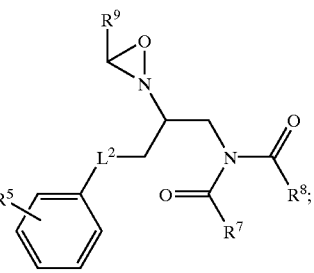

(19)

(d) reacting the product of step (c) and a compound of formula H₂NOR², or a salt thereof, and base; and (e) optionally deprotecting the product of step (d).

In a preferred embodiment the compound of formula (20) is selected from the group consisting of
3-((2S)-2-(hydroxyamino)-3-((4'-(trifluoromethoxy)(1,1'-biphenyl)-4-yl)oxy)propyl)-5,5-dimethyl-2,4-imidazolidinedione and
3-((2S)-3-(4-bromophenoxy)-2-(hydroxyamino)propyl)-5,5-dimethyl-2,4-imidazolidinedione.

Another embodiment of the instant invention comprises a process for preparing of a compound of formula (20-b)

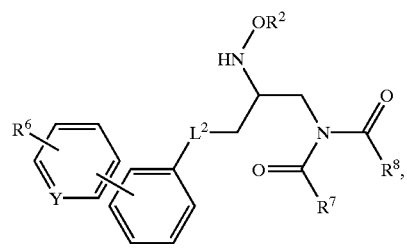

(20-b)

or a salt thereof, the process comprising:

(a) reacting the compound of formula (20-a)

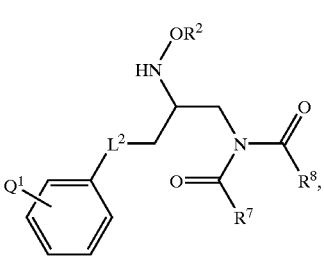

(20-a)

the coupling catalyst, and the compound of formula (6)

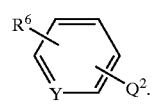

(6)

In a preferred embodiment the compound of formula (20-b) is
3-((2S)-2-(hydroxyamino)-3-((4'-(trifluoromethoxy)(1,1'-biphenyl)-4-yl)oxy)propyl)-5,5-dimethyl-2,4-imidazolidinedione.

Another embodiment of the instant invention comprises a process for preparing of a compound of formula (20-c)

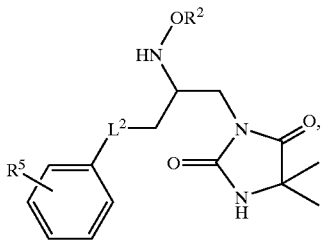

or a salt thereof, the process comprising:

(a) reacting a compound of formula (15-b)

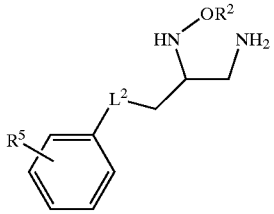

and a compound of formula (21)

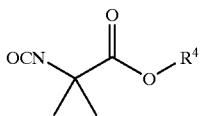

to provide a compound of formula (22)

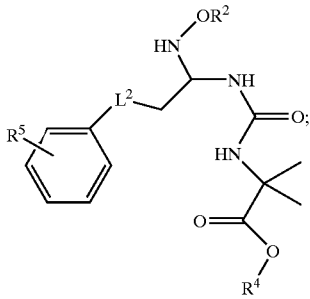

and (b) reacting the product from step (a) and acid.

In a preferred embodiment the compound of formula (20-c) is
3-((2R)-2-((benzyloxy)amino)-3-(4-bromophenoxy)propyl)-5,5-dimethyl-2,4-imidazolidinedione.

Another embodiment of the instant invention comprises a process for preparing a compound of formula (23)

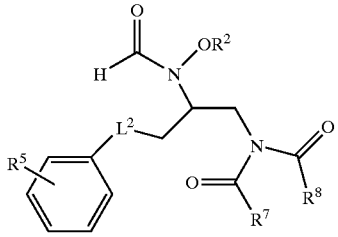

the process comprising:

(a) N-formylating the compound of formula (20); and (b) optionally deprotecting the product of step (a).

In a preferred embodiment the compound of formula (23) is selected from the group consisting of
(1S)-2-(4,4-dimethyl-2,5-dioxo-1-imidazolidinyl)-1-(((4'-(trifluoromethoxy)(1,1'-biphenyl)-4-yl)oxy)methyl)ethyl(hydroxy)formamide and
benzyloxy((1R)-2-(4-bromophenoxy)-1-((4,4-dimethyl-2,5-dioxo-1-imidazolidinyl)methyl)-ethyl)formamide.

Another embodiment of the instant invention comprises a process for preparing a compound of formula (23-b)

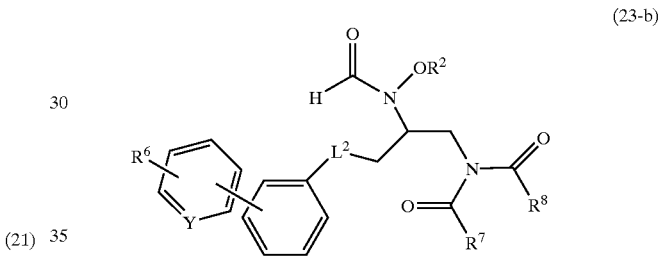

the process comprising:

(a) reacting a compound of formula (23-a)

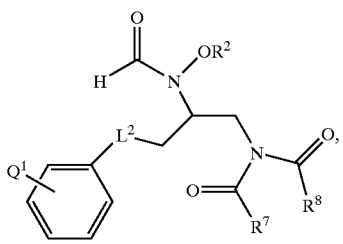

the coupling catalyst, and the compound of formula (6)

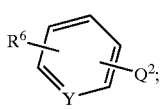

and (b) optionally deprotecting the product of step (a).

In a preferred embodiment the compound of formula (23-b) is selected from the group consisting of
4-(((2R)-2-((benzyloxy)(formyl)amino)-3-(4,4-dimethyl-2,5-dioxo-1-imidazolidinyl)-propyl)oxy)-4'-(trifluoromethoxy)-1,1'-biphenyl.

Another embodiment of the instant invention comprises a process for preparing a compound of formula (23-b)

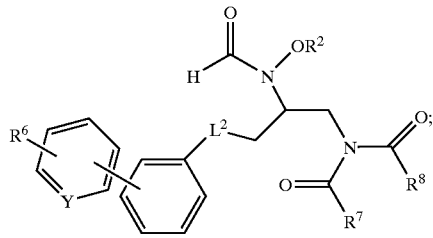
(23-b)

the process comprising:

(a) reacting a compound of formula (1)

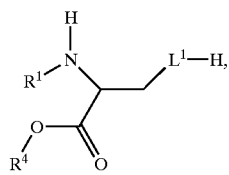
(1)

a base, and a reagent selected from the group consisting of phosgene, thiophosgene, triphosgene, carbonylduimidazole, thiocarbonyldiimidazole, and a dialkyl carbonate to provide a compound of formula (2);

(2)

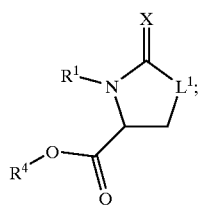

(b) reacting the product of step (a) with a reducing agent to provide a compound of formula (3);

(3)

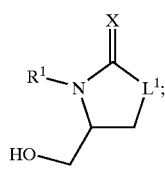

(c) activating the hydroxyl of the product of step (b);
(d) reacting the product of step (c) with base and a compound of formula (4)

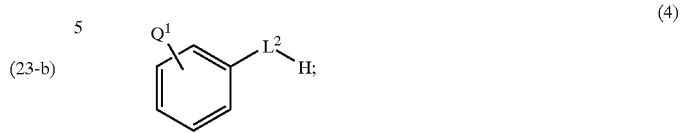
(4)

to provide a compound of formula (5-a),

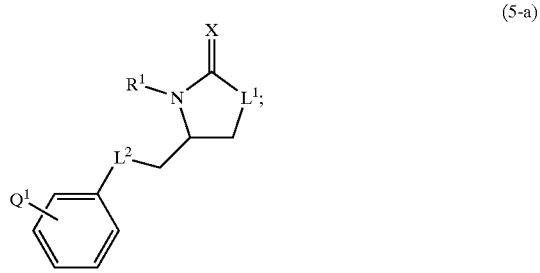
(5-a)

(e) optionally oxidizing the product of step (d);
(f) reacting the product of step (d) or step (e), a coupling catalyst, and a compound of formula (6)

(6)

to provide a compound of formula (5-b),

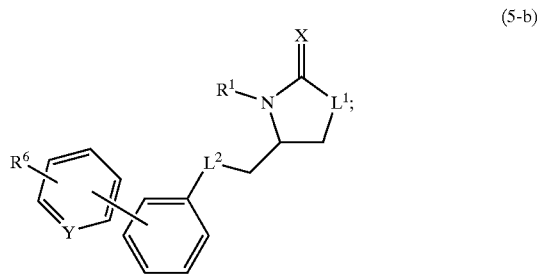
(5-b)

(g) reacting the product of step (f) with base to provide a compound of formula (15),

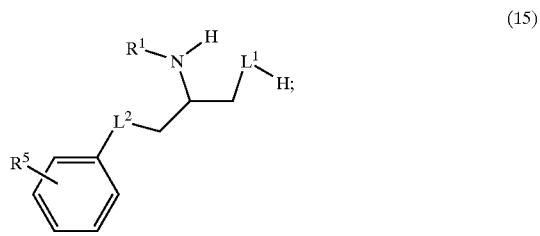
(15)

(h) reacting the product of step (g) with a compound of formula $R^9$—CHO, to provide a compound of formula (16),

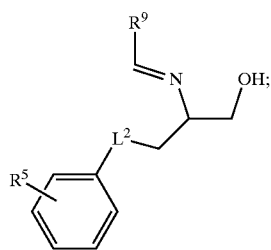

(i) reacting the product of step (h) with a compound of formula (17)

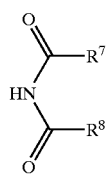

to provide a compound of formula (18)

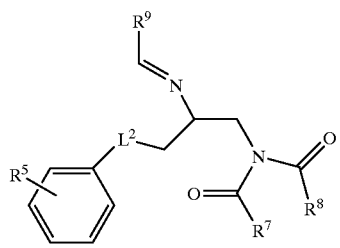

(j) reacting the product of step (i) and an oxaziridine forming agent to provide a compound of formula (19)

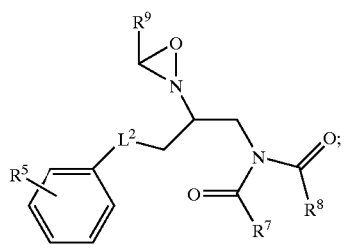

(k) reacting the product of step (j) with $H_2NOR^2$, or a salt thereof, and base to provide a compound of formula (20-b);

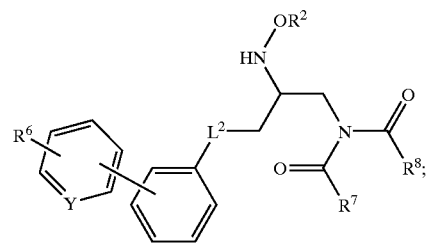

(l) N-formylating the product from step (k) to provide a compound of formula (23-b);

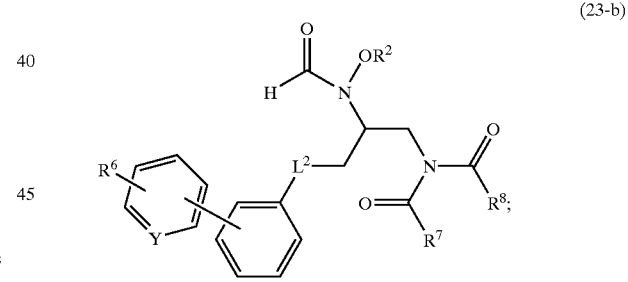

and (m) optionally deprotecting the product of step (l).

Another embodiment of the instant invention comprises a process for the preparation of a compound of formula (23-b)

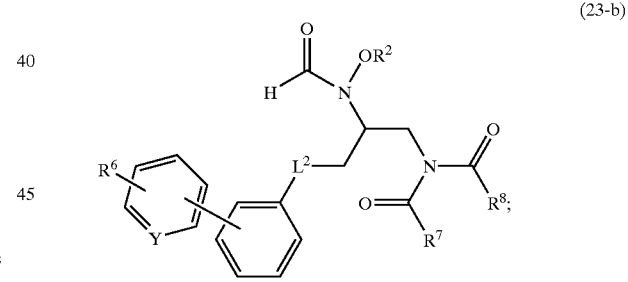

the process comprising:

(a) reacting a compound of formula (1)

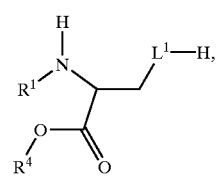

a base, and a reagent selected from the group consisting of phosgene, thiophosgene, triphosgene, carbonyldiimidazole, thiocarbonyldiimidazole, and a dialkyl carbonate, to provide a compound of formula (2);

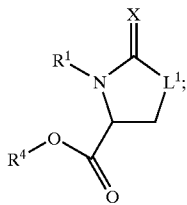
(2)

(b) reacting the product of step (a) with a reducing agent to provide a compound of formula (3);

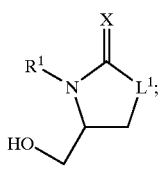
(3)

(c) activating the hydroxyl of the product of step (b);
(d) reacting the product of step (c) with base and a compound of formula (4)

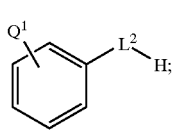
(4)

to provide a compound of formula (5-a),

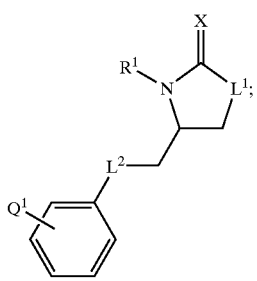
(5-a)

(e) optionally oxidizing the product of step (d);
(f) reacting the product of step (e) with base to provide a compound of formula (15),

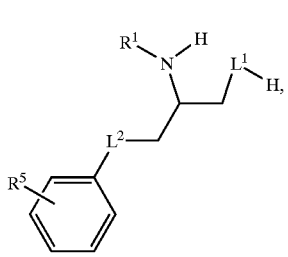
(15)

wherein
$R^5$ is $Q^1$;

(g) reacting the product of step (f) with a compound of formula $R^9$—CHO to provide a compound of formula (16),

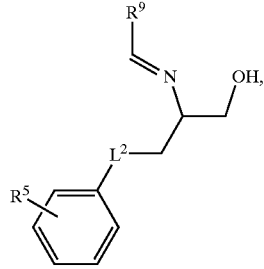
(16)

wherein
$R^5$ is $Q^1$;

(h) reacting the product of step (g) with a compound of formula (17)

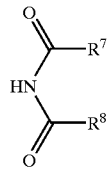
(17)

to provide a compound of formula (18)

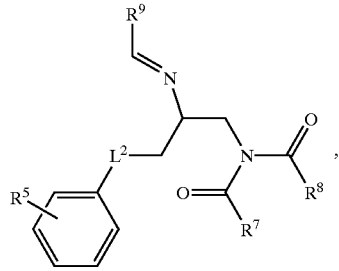
(18)

wherein $R^5$ is $Q^1$;

(i) reacting the product of step (h) with an oxaziridine forming agent to provide a compound of formula (19)

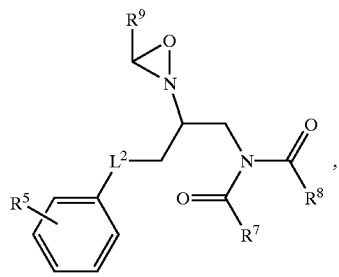
(19)

wherein
$R^5$ is $Q^1$;

(j) reacting the product of step (i) with $H_2NOR^2$, or a salt thereof, and base to provide a compound of formula (20);

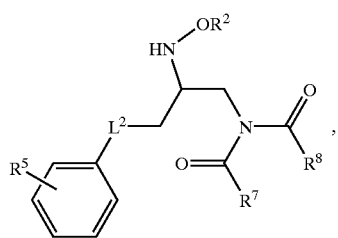
(20)

wherein
R⁵ is Q¹;

(k) reacting the product of step (j) with a coupling catalyst and a compound of formula (6)

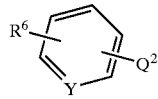
(6)

to provide a compound of formula (20),

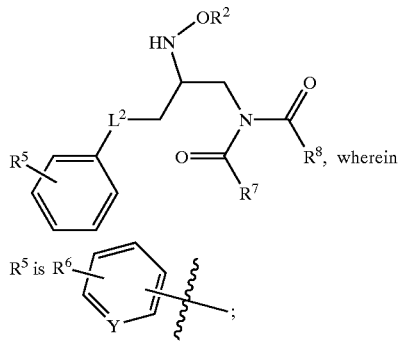
(5)

R⁸, wherein (l) N-formylating the product from step (k) to provide a compound of formula (23)

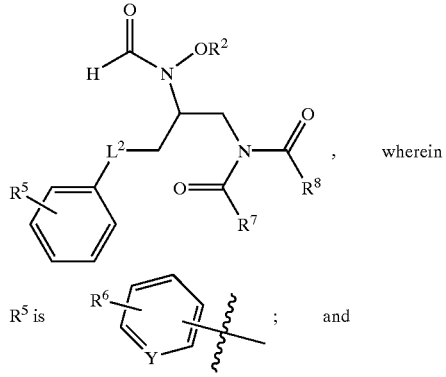
(23)

wherein and (m) optionally deprotecting the product of step (l).

Another embodiment of the instant invention comprises a process for the preparation of a compound of formula (23)

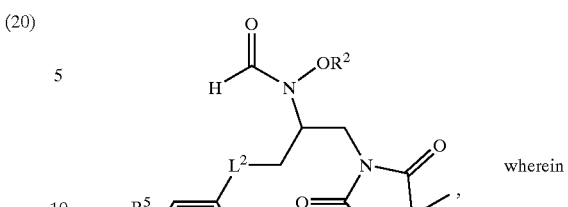
(23)

wherein

R² is hydrogen; and

R⁵ is 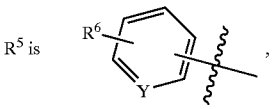, the process comprising:

(a) reacting a compound of formula (7)

(7)

a compound of formula (4)

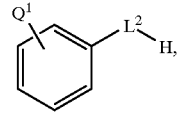
(4)

and base to provide a compound of formula (8)

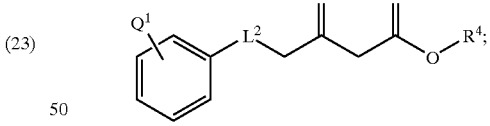
(8)

(b) optionally oxidizing the product from step (a);

(c) hydrogenating the product of step (a) or step (b) to provide a compound of formula (9)

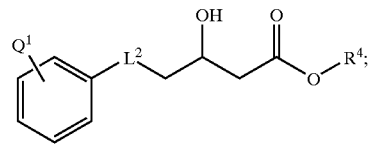
(9)

(d) reacting the product from step (c) with base to provide a compound of formula (10)

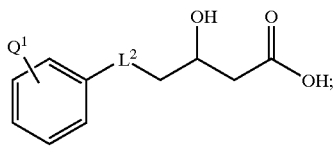
(10)

(e) reacting the product from step (d) with H₂NOR² or a salt thereof, wherein R² is a a hydroxyl protecting group, under dehydrating conditions to provide a compound of formula (11)

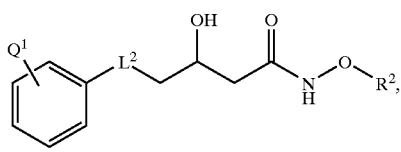
(11)

wherein
R² is a hydroxyl protecting group;

(f) reacting the product of step (e) under Mitsunobu conditions to provide a compound of formula (12)

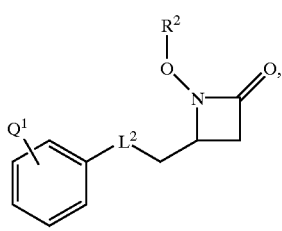
(12)

wherein
R² is a hydroxyl protecting group;

(g) reacting the product from step (f) with base to provide a compound of formula (13)

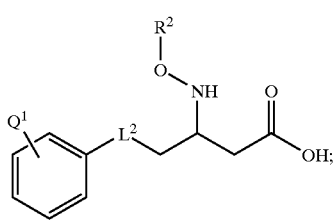
(13)

(h) activating the product from step (g) with azide to provide a compound of formula (5-c);

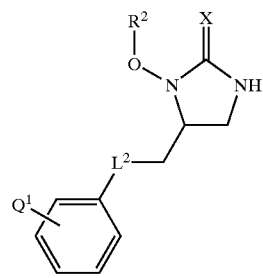
(5-c)

wherein
R² is a hydroxyl protecting group;

(i) reacting the product from step (h) with base to provide a compound of formula (15)

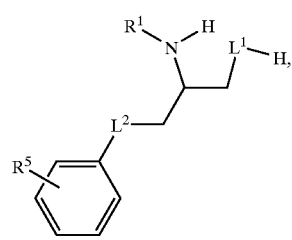
(15)

wherein
R¹ is —OR²;
R² is a hydroxyl protecting group;
R⁵ is Q¹; and
L¹ is —NH—;

(j) reacting the product from step (i) with a compound of formula (21)

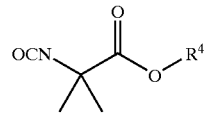
(21)

to provide a compound of formula (22)

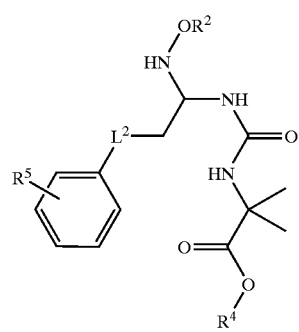
(22)

wherein

R² is a hydroxyl protecting group;

(k) reacting the product from step (j) with acid to provide a compound of formula (20-c)

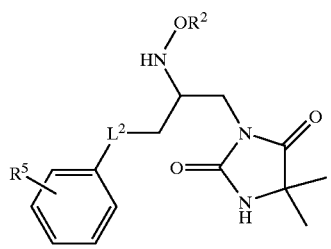
(20-c)

wherein

R² is a hydroxyl protecting group;

(l) N-formylating the product from step (k) to provide a compound of formula (23)

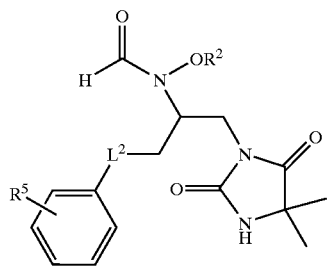
(23)

wherein

R² is a hydroxyl protecting group;

(m) reacting the product from step (l) with a coupling catalyst and a compound of formula (6)

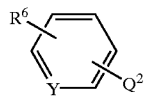
(6)

to provide a compound of formula (23)

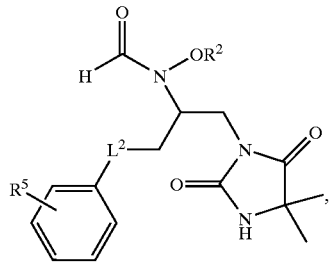
(23)

wherein

R² is a hydroxyl protecting group R⁵ is

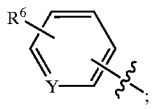;

and (n) deprotecting the product of step (m).

Detailed Description of The Invention

This invention relates to processes for the preparation of matrix metalloproteinase inhibitors and to intermediates which are useful in these processes of preparation. The following terms have the meanings specified.

The term "alkoxy," as used herein, refers to an alkyl group connected to the parent group through an oxygen atom.

The term "alkoxyalkyl," as used herein, refers to an alkyl group to which is attached at least one alkoxy group.

The term "alkyl," as used herein, refers to a monovalent straight or branched chain saturated hydrocarbon having one to six carbons.

The term "alkylsulfinyl," as used herein, refers to an alkyl group connected to the parent group through a sulfinyl group.

The term "alkylsulfonyl," as used herein, refers to an alkyl group connected to the parent group through a sulfonyl group.

The term "amino," as used herein, refers to —NH₂ or a derivative thereof formed by independent replacement of one or both hydrogens thereon by a substituent selected from the group consisting of alkyl, aryl, arylalkyl, cycloalkyl, cycloalkylalkyl, and an amino protecting group.

The term "amino protecting group," as used herein, refers to selectively removable groups which protect amino groups against undesirable side reactions during synthetic procedures and includes all conventional amino protecting groups. Examples of amino groups include optionally substituted acyl groups such as trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, and 8-quinolyloxycarbonyl; optionally substituted arylalkyl groups such as benzyl, diphenylmethyl, and triphenylmethyl; optionally substituted arylthio groups such as 2-nitrophenylthio and 2,4-dinitrophenylthio; optionally substituted alkyl sulfonyl and optionally substituted arylsulfonyl groups such as methanesulfonyl, and para-toluenesulfonyl; optionally substituted dialkylaminoalkylidene groups such as N,N-dimethylaminomethylene; optionally substituted arylalkylidene groups such as benzylidene, 2-hydroxybenzylidene, 2-hydroxy-5-chlorobenzylidene, and 2-hydroxy-1-naphthylmethylene; optionally substituted nitrogen-containing heterocyclic alkylidene groups such as 3-hydroxy-4-pyridylmethylene; optionally substituted cycloalkylidene groups such as cyclohexylidene, 2-ethoxycarbonylcyclohexylidene, 2-ethoxycarbonylcyclopentylidene, 2-acetylcyclohexylidene, and 3,3-dimethyl-5- oxycyclohexylidene; optionally substituted diarylalkylphosphoryl and optionally substituted diarylalkylphosphoryl groups such as diphenylphosphoryl and dibenzylphosphoryl; optionally substituted oxygen-containing heterocyclic alkyl groups such as 5-methyl-2-oxo-2H-1,3-dioxol-4-yl-methyl; and optionally substituted silyl groups such as trimethylsilyl, triethylsilyl, and triphenylsilyl.

The term "aminosulfonyl as used herein, refers to an amino group connected to the parent group through a sulfonyl group.

The term "aryl," as used herein, refers to a mono or bicyclic carbocyclic ring system having at least one aromatic ring. Aryl groups are exemplified by phenyl, naphthyl, 1,2-dihydronaphthyl, 1,2,3,4-tetrahydronaphthyl, fluorenyl, indanyl, and indenyl.

The term "aryl," as used herein, also includes compounds of formula

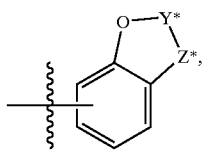

wherein Y* is —C(O)— or —(CH$_2$)$_v$—, wherein v is 1 or 2; and Z* is —CH$_2$— or —O—. The aryl groups of this invention can be optionally substituted with one, two, or three substituents independently selected from the group consisting of alkoxy, alkyl, halo, and thioalkoxy.

The term "arylalkyl," as used herein, refers to an alkyl group to which is attached at least one aryl group.

The term "base," as used herein, refers to a reagent capable of accepting protons during the course of a reaction. Examples of bases include carbonates such as potassium carbonate, potassium bicarbonate sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; trialkylamines such as triethylamine and diisopropylamine; heterocyclic amines such as imidazole, pyridine, pyridazine, pyrimidine, and pyrazine; bicyclic amines such as DBN and DBU; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "carbonyl," as used herein, refers to —C(=O)—.

The term "carboxaldehyde," as used herein, refers to —CHO.

The term "carboxy," as used herein, refers to —CO$_2$H.

The term "carboxyl protecting group," as used herein, refers to selectively removable groups which protect hydroxyl groups against undesirable side reactions during synthetic procedures and includes all conventional carboxyl protecting groups. Examples of carboxyl groups include optionally substituted alkyl groups such as methyl, ethyl, n-propyl, isopropyl, 1,1-dimethylpropyl, n-butyl, and tert-butyl; aryl groups such as phenyl, and naphthyl; optionally substituted arylalkyl groups such as benzyl, diphenylmethyl, triphenylmethyl, para-nitrobenzyl, para-methoxybenzyl, and bis(para-methoxyphenyl)methyl; optionally substituted acylalkyl groups such as acetylmethyl, benzoylmethyl, para-nitrobenzoylmethyl, para-bromobenzoylmethyl, and para-methanesulfonylbenzoylmethyl; optionally substituted oxygen-containing heterocyclic groups such as 2-tetrahydropyranyl and 2-tetrahydrofuranyl; optionally substituted haloalkyl groups such as 2,2,2-trichloroethyl; optionally substituted alkylsilylalkyl groups such as 2-(trimethylsilyl)ethyl; optionally substituted acyloxyalkyl groups such as acetoxymethyl, propionyloxymethyl, and pivaloyloxymethyl; optionally substituted nitrogen-containing heterocyclic groups such as phthalimidomethyl and succinimidomethyl; optionally substituted cycloalkyl groups such as cyclopropyl, cyclobutyl, cyclopentyl, and cyclohexyl; optionally substituted alkoxyalkyl groups such as methoxymethyl, methoxyethoxymethyl, and 2-(trimethylsilyl)ethoxymethyl; optionally substituted arylalkoxyalkyl groups such as benzyloxymethyl; optionally substituted alkylthioalkyl groups such as methylthiomethyl and 2-methylthioethyl; optionally substituted arylthioalkyl groups such as phenylthiomethyl; optionally substituted alkenyl groups such as 1,1-dimethyl-2-propenyl, 3-methyl-3-butenyl, and allyl; and optionally substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "coupling catalyst," as used herein, refers to palladium complexes which enhance the rate of biaryl couplings. Examples of catalysts include palladium(II) acetate, tetrakis(triphenylphosphine)palladium(0), Pd$_2$Cl$_2$ (dba), and PdCl$_2$.CH$_2$Cl$_2$. Each of these catalysts can be used with an additive such as triphenylphosphine, triphenylarsine, or a trialkylphosphine such as tributylphosphine optionally present.

The term "cyano," as used herein, refers to —CN.

The term "cyanoalkyl," as used herein, refers to an alkyl group to which is attached at least one cyano group.

The term "cycloalkyl," as used herein, refers to a saturated cyclic alkyl group having three to six carbons.

The term "cycloalkylalkoxy," as used herein, refers to an alkoxy group to which is attached at least one cycloalkyl group.

The term "cycloalkylalkyl," as used herein, refers to an alkyl group to which is attached at least one cycloalkyl group.

The terms "halo" or "halide," as used herein, refer to F, Cl, Br, or I.

The term "haloalkyl," as used herein, refers to an alkyl group to which is attached at least one halide.

The term "heterocycle," as used herein, refers to five- or six-membered saturated or unsaturated rings having one, two, or three heteroatoms independently selected from the group consisting of nitrogen, oxygen, and sulfur. The nitrogen and sulfur heteroatoms can be optionally oxidized, and the nitrogen heteroatoms can be optionally quaternized. The heterocycles of the instant invention are attached through a carbon atom in the ring. Representative heterocycles include pyrrolidinyl, piperidinyl, pyrazinyl, pyrazolyl, pyridazinyl morpholinyl, piperazinyl, thiomorpholinyl, pyridyl, pyrimidinyl, quinolyl, furyl, benzofuryl, thienyl, thiazolyl, pyrimidyl, indolyl, imidazolyl, isothiazolyl, isoxazolyl, oxadiazolyl, oxazolyl, 1,2,3-oxadiazolyl, thienyl, triazolyl, 1,3,4-thiadiazolyl, and tetrazolyl.

The term "(heterocycle)oxy," as used herein, refers to a heterocycle attached to the parent group through an oxygen atom.

The term "(heterocycle)oxyalkyl," as used herein, refers to an alkyl group to which is attached at least one (heterocycle)oxy group.

The term "hydroxy," as used herein, refers to —OH.

The term "hydroxy protecting group," as used herein, refers to selectively introducible and movable groups which protect hydroxyl groups against undesirable side reactions during synthetic procedures. Examples of hydroxyl protecting groups include optionally substituted acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, and benzoyl; optionally substituted alkyl groups such as methyl, tert-butyl, 2,2,2-trichloroethyl, and 2-trimethylsilylethyl; optionally substituted alkenyl groups such as as 1,1-dimethyl-2-propenyl, 3-methyl-3-butenyl, and allyl; optionally substituted arylalkyl groups such as benzyl, para-methoxybenzyl, 3,4-dimethoxybenzyl, diphenylmethyl, and triphenylmethyl; oxygen-containing and sulfur-containing heterocyclic groups such as tetrahydrofuryl, tetrahydropyranyl, and tetrahydrothiopyranyl; optionally substituted alkoxy and optionally substituted alkylthioalkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, and 1-ethoxyethyl; alkylsulfonyl; optionally substituted arylsulfonyl groups such as methanesulfonyl, and para-toluenesulfonyl; and optionally substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "hydroxyalkyl," as used herein, refers to an alkyl group to which is attached at least one hydroxy group.

The term "methine," as used herein, refers to =C(H)—.

The term "Mitsunobu conditions," as used herein, refers to treatment of an alcohol with a diazo compound such as DIAD or DEAD and a triarylphosphine such as triphenylphosphine or a trialkylphosphine such as tributylphosphine.

The term "pharmaceutically acceptable salt," as used herein, refers to salts which are suitable for use in contact with tissue without undue toxicity, irritation, or allergic response and are commensurate with a reasonable benefit/risk ratio. The salts can be prepared during the final isolation and purification of the compounds or separately by reacting a basic group with a suitable acid. Representative acid addition salts include acetate, adipate, alginate, citrate, aspartate, benzoate, benzenesulfonate, sulfate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, para-toluenesulfonate and undecanoate. Basic nitrogen-containing groups can also be quatemized with alkyl halides such as methyl, ethyl, propyl, and butyl chlorides, bromides, and iodides; dialkyl sulfates such as dimethyl, diethyl, dibutyl and diamyl sulfates; long chain halides such as decyl, lauryl, myristyl, and stearyl chlorides, bromides, and iodides; and arylalkyl halides such as benzyl and phenethyl bromides. Examples of acids employed to form pharmaceutically acceptable acid addition salts include inorganic acids such as hydrochloric, hydrobromic, sulfuric, and phosphoric and organic acids as oxalic, maleic succinic, and citric.

Basic addition salts can be prepared during the final isolation and purification of the compounds by reacting a carboxylic acid-containing group with a suitable base such as the hydroxide, carbonate, or bicarbonate of a pharmaceutically acceptable metal cation or with ammonia or an organic primary, secondary, or tertiary amine. Pharmaceutically acceptable salts include cations based on alkali metals or alkaline earth metals such as lithium, sodium, potassium, calcium, magnesium, and aluminum salts and nontoxic quaternary ammonia and amine cations such as ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrugs," as used herein, refers to prodrugs and zwitterionic forms of the compounds which are suitable for contact with tissue without undue toxicity, irritation, allergic response, are commensurate with a reasonable benefit/risk ratio, and are effective for their intended use.

The term "phenoxy," as used herein, refers to a phenyl group connected to the parent group through an oxygen atom.

The term "phenoxyalkyl," as used herein, refers to an alkyl group to which is attached at least one phenoxy group.

The term "phenylalkoxy," as used herein, refers to to an alkoxy group to which is attached at least one phenyl group.

The term "phenylalkoxyalkyl," as used herein, refers to an alkyl group to which is attached at least one phenylalkoxy group.

The term "perfluoroalkoxy," as used herein, refers to a perfluoroalkyl group attached to the parent group through an oxygen atom.

The term "perfluoroalkyl," as used herein, refers to an alkyl group in which all of the hydrogen atoms have been replaced with fluoride atoms.

The term "perfluoroalkoxyalkyl," as used herein, refers to an alkyl group to which is attached at least one perfluoroalkoxy group.

The term "perfluorothioalkoxy," as used herein, refers to a perfluoroalkyl group attached to the parent group through a sulfur atom.

The term "perfluorothioalkoxyalkyl," as used herein, refers to an alkyl group to which is attached at least one perfluorothioalkoxy group.

The term "prodrug," as used herein, refers to compounds which are rapidly transformed in vivo to parent compounds such as, for example, by hydrolysis in blood.

The term "reducing agent," as used herein, refers to reagents capable of converting protected carboxylic acids to alcohols. Examples of reducing agents include borane-dimethylsulfide, borane-tetrahydrofuran, and sodium borohydride.

The term "sulfinyl," as used herein, refers to —S(O)—.

The term "sulfonyl," as used herein, refers to —SO$_2$—.

The term "thioalkoxy," as used herein, refers to an alkyl group attached to the parent molecular group through a sulfur atom.

The term "thioalkoxyalkyl," as used herein, refers to an alkyl group to which is attached at least one thioalkoxy group.

Asymmetric centers exist in the compounds of the invention. The invention contemplates stereoisomers and mixtures thereof. Individual stereoisomers of compounds are prepared by synthesis from starting materials containing the chiral centers or by preparation of mixtures of enantiomeric products followed by separation such as conversion to a mixture of diastereomers followed by separation or recrystallization, chromatographic techniques, or direct separation of the enantiomers on chiral chromatographic columns. Starting compounds of particular stereochemistry are either commercially available or are made by the processes described herein and resolved by techniques well-known in the art.

Chiral purity (percent enantiomeric excess (ee)) was determined by chiral HPLC (Chiralcel OD) by comparing the enantiomeric purity of a compound from a reaction mixture to a mixture of the same enantiomer in known enantiomeric excess.

Yields of compounds in solution were determined by HPLC by comparing the amount of product in solution to solutions of known concentrations of that product.

Percentages obtained by HPLC analyses were determined by peak area calculations.

All of the processes of the invention can be conducted as continuous processes. The term "continuous process," as used herein, refers to the conduction of steps in without isolation of intermediates.

The formylation process used in the synthesis of Example 1N is that described in pending U.S. application Ser. No. 09/539,950, filed on the same day herewith, incorporated herein by reference.

Abbreviations

Abbreviations which have been used in the descriptions of the scheme and the examples that follow are: DBN for 1,5-diazabicyclo[4.3.0]non-5-ene; DBU for 1,8-diazabicyclo[5.4.0]undec-7-ene; dba for dibenzylideneacetone; DIAD for diisopropyl azodicarboxylate; DEAD for diethyl azodicarboxylate; THF for tetrahydrofuran; dppf for diphenylphosphinoferrocene; DMF for dimethylformamide; DME for dimethoxyethane; DMSO for dimethylsulfoxide; BINAP for 2,2'-bis(diphenylphosphino)-1,1'-binaphthyl; DCC for 1,3-dicyclohexylcarbodiimide; DIC for 1,3-diisopropylcarbodiimide; HOBT for 1-hydroxybenzotriazole hydrate; EDCI for 1-(3-dimethylaminopropyl)-3-ethylcarbodiimide hydrochloride; PyBOP benzotriazol-1-yloxytripyrrolidinophosphonium hexafluorophosphate; NMM for N-methylmorpholine; NMP for 1-methyl-2-pyrrolidinone; MTBE for methyl tert-butyl ether; m-CPBA for 3-chloroperoxybenzoic acid; and DPPA for diphenylphosphoryl azide.

Synthetic Processes

The processes and compounds and of the instant invention will be better understood in connection with the following synthetic schemes. The compounds can be prepared by a variety of processes, and representative processes are shown in Schemes 1–9. The groups $R^1$–$R^9$, $L^1$, $L^2$, X, and $Q^1$ are defined previously. It will be readily apparent to one skilled in the art that the selective protection and deprotection steps, as well as the order of the steps themselves, can be carried out in varying order, depending on the nature of $R^1$–$R^9$, $L^1$, $L^2$, X, and $Q^1$, to successfully complete the syntheses shown below.

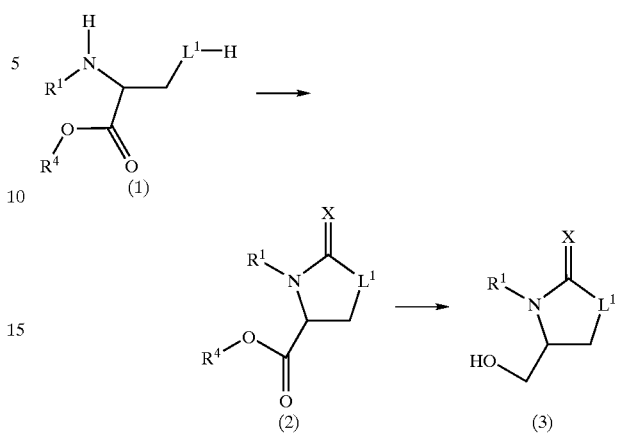

Scheme 1

As shown in Scheme 1, compounds of formula (1) can be converted to compounds of formula (2) (X is O or S) by treatment of the former with an acylating agent and base. Representative acylating agents include phosgene, triphosgene, carbonyldiimidazole, dialkyl carbonates (for X is O), thiophosgene and thiocarbonyldiimidazole (for X is S). Representative bases include triethylamine, diisopropylethylamine, pyridine, and imidazole.

Solvents used in these reactions include dichloromethane, carbon tetrachloride, 1,2-dichloroethane, and chloroform, although dialkyl carbonates can themselves be used as solvents. The reaction temperature is about –10° C. to about 100° C. and depends on the method chosen. Reaction times are typically about 0.5 to about 24 hours. In a preferred embodiment, compounds of formula (1) in dichloromethane at 0° C. are treated with triphosgene and triethylamine and stirred for 7 hours to provide compounds of formula (2).

Conversion of compounds of formula (2) to compounds of formula (3) can be accomplished by treatment of the former with a reducing agent such as sodium borohydride, lithium aluminum hydride, sodium triacetoxy-borohydride, and lithium tri-tert-butoxyaluminum hydride. Solvents used in these reactions include ethanol, methanol, THF, and diethyl ether. The reaction temperature is about –78° C. to about 35° C. and depends on the process chosen. Reaction times are typically 1 to 24 hours. In a preferred embodiment, compounds of formula (2) in ethanol at 0° C. are treated with sodium borohydride and stirred for 5 hours. The reaction is quenched to a pH of between to provide compounds of formula (3).

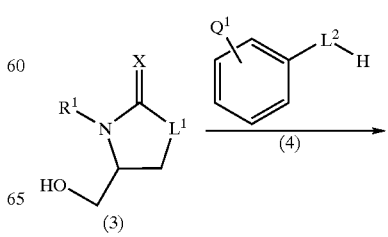

Scheme 2

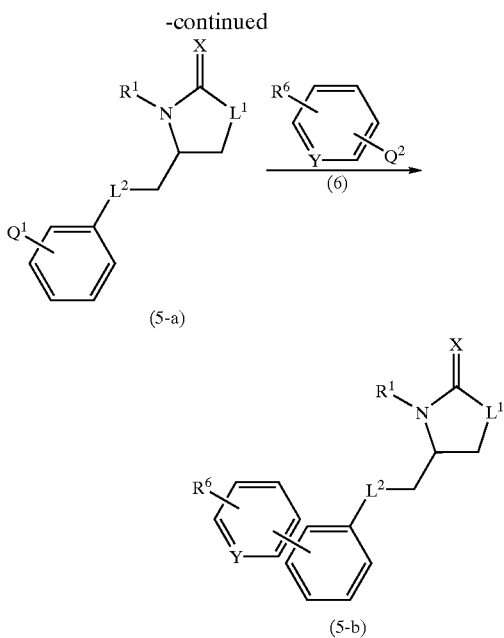

(5-a)

(5-b)

As shown in Scheme 2, compounds of formula (3) can be converted to compounds of formula (5-a) by activation of the hydroxyl group of the former followed by treatment with compounds of formula (4) and base. Activation of the hydroxyl group can be accomplished by treatment with an acylating or sulfonating agent and base. Representative acylating and sulfonating agents include para-toluenesulfonyl chloride, benzenesulfonyl chloride, trifluoroacetic anhydride, and methanesulfonyl chloride. Examples of bases include pyridine, imidazole, diisopropylethylamine, and triethylamine. Solvents used in these reactions include dichloromethane, chloroform, THF, and methyl tert-butyl ether. The reaction temperature is about −10° C. to about 50° C. and depends on the process chosen. Reaction times are typically about 1 to about 24 hours. The products can then be treated with compounds of formula (4) ($L^2$ is O or S; $Q^1$ is halide, methanesulfonate, or para-toluenesulfonate) and base to provide compounds of formula (5-a). Representative bases include potassium carbonate, sodium carbonate, lithium hexamethyldisilazide, and lithium diisopropylamide. Examples of solvents used in these reactions include acetonitrile, water, THF, diethyl ether, and mixtures thereof. The reaction temperature is about 25° C. to about 100° C. and depends on the process chosen. Reaction times are typically about 2 to about 36 hours. In a preferred embodiment, compounds of formula (3) in pyridine at 5° C. are treated with para-toluenesulfonyl chloride, warmed to room temperature, and stirred for 16 hours. The products in acetonitrile at 70° C. are treated with compounds of formula (4) and potassium carbonate to provide compounds of formula (5-a).

Conversion of compounds of formula (5-a) to compounds of formula (5-b) can be accomplished by treatment of the former with a compound of formula (6) (Y is nitrogen or methine; $Q^2$ is trialkylstannane, boronic acid, boronic ester, magnesium halide, zinc halide, or silyl(alkyl)cyclobutane) and a coupling catalyst. Representative coupling catalysts include $Pd(PPh_3)_4$, $Pd(PPh_3)_2Cl_2$, $Pd(dppf)Cl_2$, $Ni(PPh_3)_4$, and $Pd(OAc)_2$. Examples of solvents used in these reactions include THF, water, acetonitrile, dichloromethane, DMF, DME, and mixtures thereof. The reaction temperature is about 25° C. to about 120° C. and depends on the process chosen. Reaction times are typically about 0.5 to about 36 hours. In a preferred embodiment, compounds of formula (5-a) in THF and water are treated with potassium phosphate and a compound of formula (6) (Y is CH; $Q^2$ is boronic acid), heated to 65° C., and stirred for 1 hour to provide compounds of formula (5-b).

Scheme 3

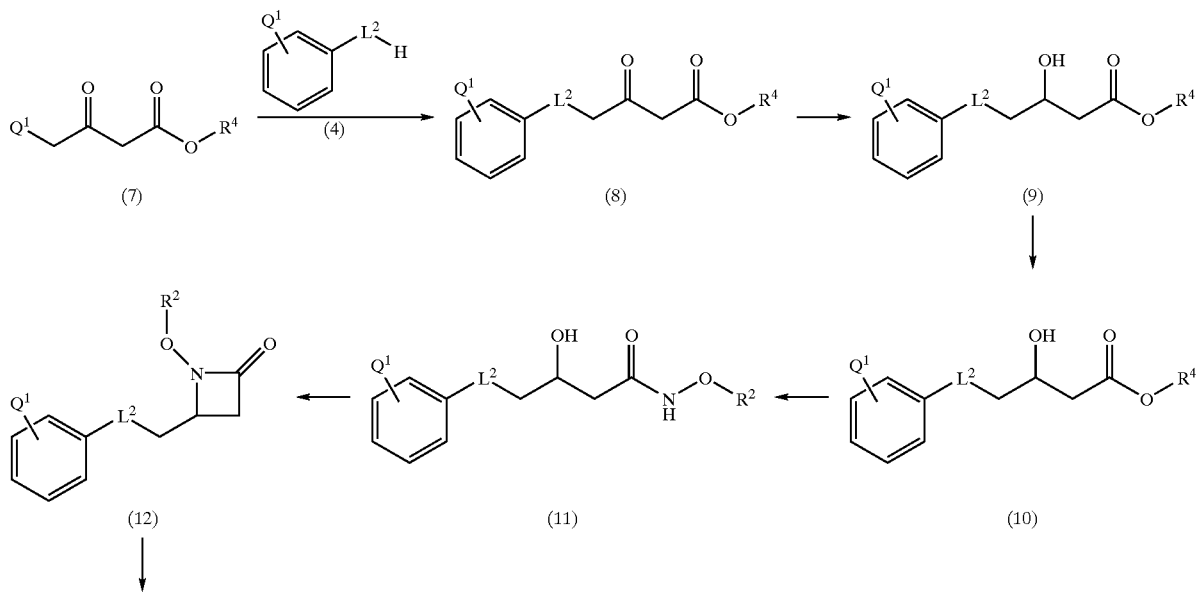

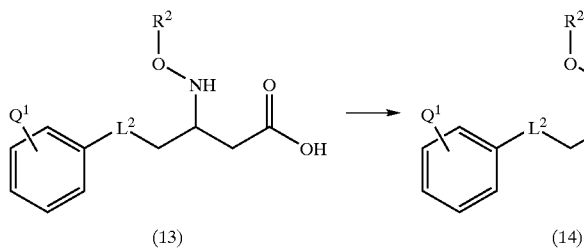
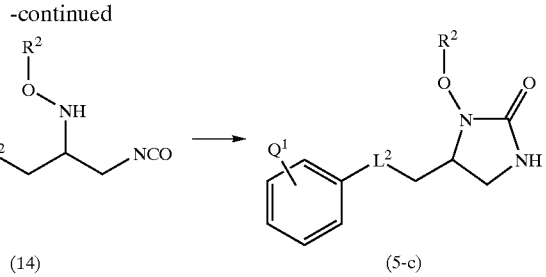

As shown in Scheme 3, compounds of formula (7) can be treated with compounds of formula (4) and base to provide compounds of formula (8). Representative bases include sodium hydroxide, sodium carbonate, potassium carbonate, and lithium hexamethyldisilazide. Examples of solvents used in these reactions include DMSO, water, acetonitrile, THF, and mixtures thereof. The reaction temperature is about –10° C. to 50° C. and depends on the process chosen. Reaction times are typically 0.5 to 12 hours. In a preferred embodiment, compounds of formula (7) ($Q^1$ is Cl, $R^4$ is alkyl) in DMSO and water at room temperature are treated with a compound of formula (4) ($L^2$ is O and $Q^1$ is Br) and NaOH for 1 hour to provide compounds of formula (8).

Conversion of compounds of formula (8) to compounds of formula (9) can be accomplished by hydrogenation and $(Ru_2Cl_5(R)BINAP_2)^-Et_2NH_2^+$. Examples of solvents used in this reaction include ethanol, methanol, propanol, and tert-butanol. The reaction temperature is about 50° C. to 150° C. and depends on the process chosen. Reaction times are about 1–24 hours. In a preferred embodiment, compounds of formula (3) in ethanol are treated with $(Ru_2Cl_5(R)BINAP_2)^-Et_2NH_2^+$ and 2M HCl and heated to 100° C. under hydrogen for 8 hours to provide compounds of formula (9).

Compounds of formula (9) ($R^4$ is alkyl) can be converted to compounds of formula (10) ($R^4$ is H) by treatment with aqueous base, followed by treatment with aqueous acid. Representative bases include sodium hydroxide, potassiym hydroxide, and lithium hydroxide. Examples of acids used in these reactions are hydrochloric acid, acetic acid, nitric acid, and sulfuric acid. Solvents used in these reactions include isopropanol, isopropanol acetate, ethyl acetate, ethanol, methanol, and mixtures thereof. The reaction temperature is about 0° C. to 25° C. and depends on the process chosen. Reaction times are typically 10 minutes to 24 hours. In a preferred embodiment, compounds of formula (9) in ethanol at 5° C. are treated with aqueous potassium hydroxide over 10 minutes, warmed to room temperature, treated with water and isopropyl acetate, cooled to 5° C., and treated with 6M hydrochloric acid to provide compounds of formula (10).

Conversion of compounds of formula (10) to compounds of formula (11) can be accomplished by coupling with an appropriately substituted hydroxylamine and a carbonyl activating group such as DCC, DIC, HOBT, EDCI, and PyBOP, and base. Representative bases include NMM, diisopropylethylamine, and DBU. Examples of solvents used in these reactions include dichloromethane, chloroform, DMF, THF, and NMP. The reaction temperature is about –10° C. to 60° C. and depends on the process chosen. Reaction times are typically 0.5–24 hours. In a preferred embodiment, compounds of formula (10) in DMF at 5° C. are treated with EDCI, HOBT, NMM, and O-benzylhydroxylamine hydrochloride, warmed to room temperature, and stirred for 30 minutes to provide compounds of formula (11).

Compounds of formula (11) can be converted to compounds of formula (12) by treatment with a diazo compound and a triaryl- or trialkylphosphine. Representative diazo compounds include DIAD and DEAD, while representative phosphines include triphenylphosphine and tributylphosphine. Examples of solvents used in these reactions are THF, MTBE, diethyl ether, and DME. The reaction temperature is about 20° C. to 70° C. and depends on the process chosen. The reaction time is typically 0.5 to 3 hours. In a preferred embodiment, compounds of formula (11) in THF at 40° C. are treated with DEAD and triphenylphosphine and stirred for 2 hours to provide compounds of formula (12).

Conversion of compounds of formula (12) to compounds of formula (13) can be accomplished by treatment with an aqueous hydroxide base. Representative bases include sodium hydroxide, lithium hydroxide, and potassium hydroxide. Examples of solvents used in these reactions include toluene, hexanes, benzene, THF, water, and mixtures thereof. The reaction temperature is about 30° C. to 80° C. and depends on the process chosen. Reaction times are typically 1 to 24 hours. In a preferred embodiment, compounds of formula (12) in toluene are treated with aqueous lithium hydroxide, heated to 60° C. for 3 hours, cooled to room temperature, and stirred for 16 hours to provide compounds of formula (13).

Compounds of formula (13) can be converted to compounds of formula (14) by treatment with diphenylphosphoryl azide and base. Representative bases include diisopropylethyl amine, triethylamine, and pyridine. Examples of solvents used in these reactions include THF, diethyl ether, MTBE, and dioxane. The reaction temperature is about 25° C. to 100° C. and depends on the process chosen. Reaction times are typically 1 to 24 hours. In a preferred embodiment, compounds of formula (13) in THF are treated with diphenylphosphoryl azide and diisopropylethyl amine, heated to reflux, and stirred for 3 hours to provide compounds of formula (14), which cyclize under the reaction conditions to provide compounds of formula (5-c).

Scheme 4

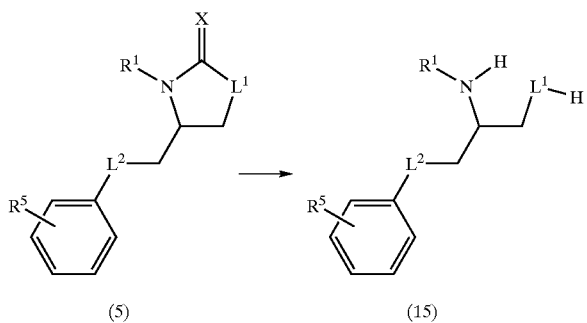

As shown in Scheme 4, compounds of formula (5) can be converted to compounds of formula (15) by treatment with base. Representative bases include potassium hydroxide, sodium hydroxide, and lithium hydroxide. Examples of solvents used in these reactions include water, THF, acetonitrile, and mixtures thereof. The reaction temperature is about 30° C. to 120° C. and depends on the process chosen. Reaction times are typically 1 to 24 hours. In a preferred embodiment, compounds of formula (5) in water are treated with potassium hydroxide, heated to reflux, and stirred for 9 hours to provide compounds of formula (15).

treated with an aldehyde ($R^9CHO$) and heated to 80° C. for 2 hours to provide compounds of formula (16).

Conversion of compounds of formula (16) to compounds of formula (18) can be accomplished by treatment with compounds of formula (17) and a diazo compound and a triaryl- or trialkylphosphine. Representative diazo compounds include DIAD and DEAD, while representative phosphines include triphenylphosphine and tributylphosphine. Examples of solvents used in these reactions are THF, MTBE, diethyl ether, and DME. The reaction temperature is about −10° C. to 35° C. and depends on the process chosen. Reaction times are typically 0.5 to 12 hours. In a preferred embodiment, compounds of formula (16) in THF at 1° C. are treated with compounds of formula (17), DIAD, and triphenylphosphine over 1.25 hours to provide compounds of formula (18).

Compounds of formula (18) can be converted to compounds of formula (19) by treatment with an oxidizing agent. Representative oxidizing agents include m-CPBA, trifluoroperacetic acid, and 2,5-dinitroperoxybenzoic acid. Examples of solvents used in these reactions include MTBE, THF, and diethyl ether. The reaction temperature is about −78° C. to 35° C. and depends on the process chosen. Reaction times are typically 0.5 to 4 hours. In a preferred embodiment, compounds of formula (18) in THF at −45° C. are treated with m-CPBA and warmed to 0° C. over 2 hours to provide compounds of formula (19).

Scheme 5

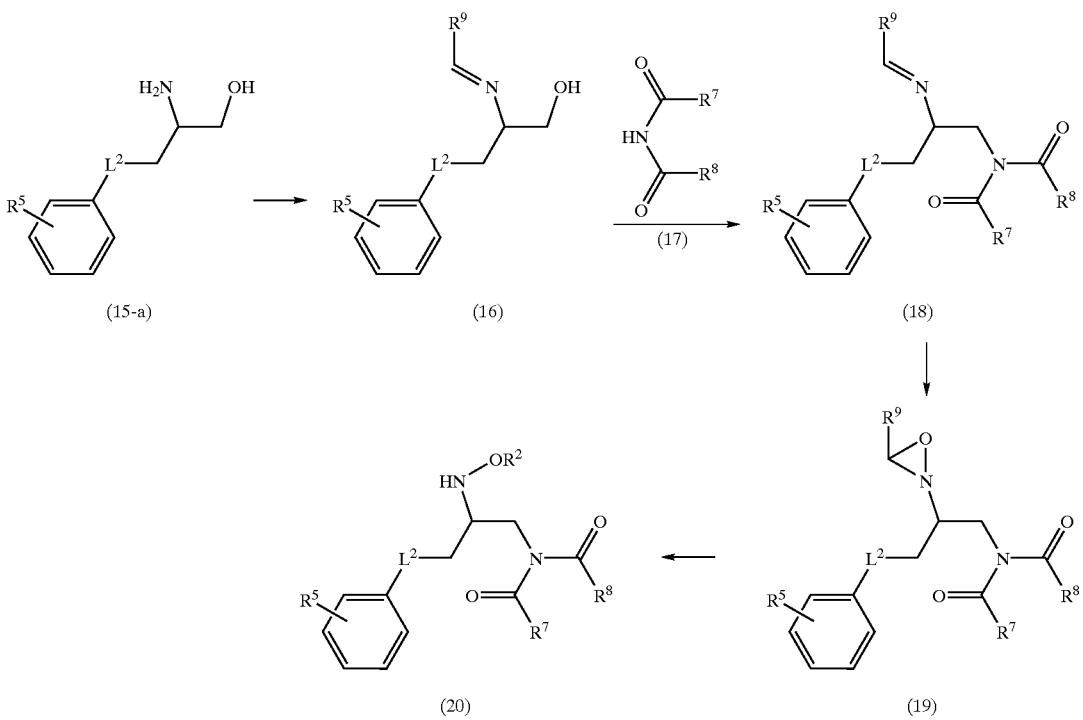

As shown in Scheme 5, compounds of formula (15-a) can be converted to compounds of formula (16) by treatment with an appropriately substituted aldehyde ($R^9CHO$). Examples of solvents used in this reaction include toluene, hexanes, heptane, and benzene. The reaction temperature is about 30° C. to 120° C. and depends on the process chosen. Reaction times are about 1 to 36 hours. In a preferred embodiment, compounds of formula (15-a) in toluene are Conversion of compounds of formula (19) to compounds of formula (20) can be accomplished by treatment with N-hydroxylamine followed by treatment with aqueous base. Representative bases include sodium hydroxide, potassium hydroxide, and lithium hydroxide. Examples of solvents used in this reaction include water, THF, dioxane, and mixtures thereof. The reaction temperature is about −10° C. to 35° C. and depends on the process chosen. Reaction times are typically 0.5 to 48 hours. In a preferred embodiment, compounds of formula (19) in THF at 1° C. are treated with N-hydroxylamine hydrochloride in water over 1 hour, warmed to room temperature, and stirred for 18 hours to provide compounds of formula (20).

Scheme 6

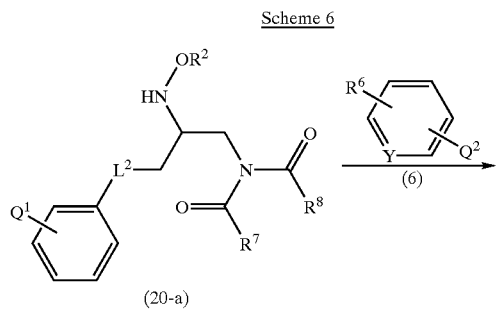

(20-a)

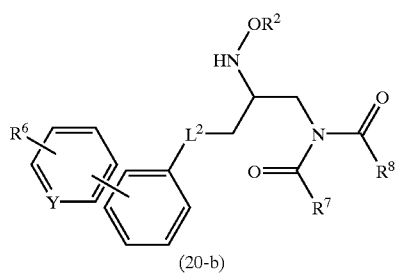

(20-b)

As shown in Scheme 6, compounds of formula (20-a) can be converted to compounds of formula (20-b) by the procedure described in Scheme 2.

Scheme 7

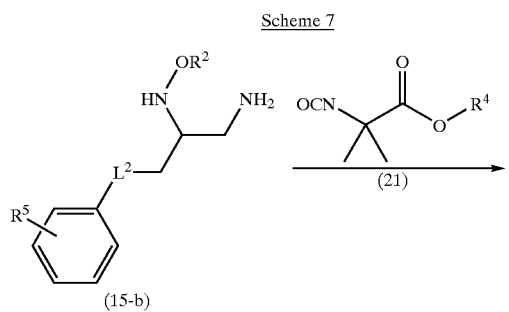

(15-b)

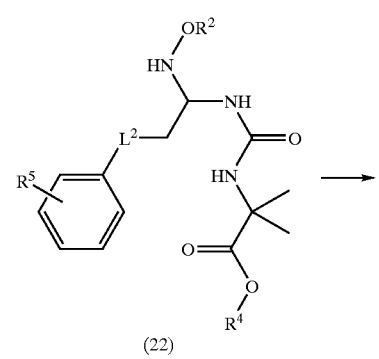

(22)

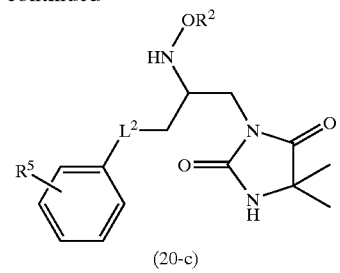

(20-c)

As shown in Scheme 7, compounds of formula (15-b) can be converted to compounds of formula (22) by treatment with compounds of formula (21). Examples of solvents used in this reaction include THF, diethyl ether, MTBE, and dioxane. The reaction temperature is about 20° C. to 40° C. and depends on the process chosen. Reaction times are typically 0.5 to 12 hours. In a preferred embodiment, compounds of formula (15-b) in THF at room temperature are treated with compounds of formula (21) and stirred for 0.5 hours to provide compounds of formula (22).

Coversion of compounds of formula (22) to compounds of formula (20-c) can be accomplished by treatment with acid. Representative acids include hydrochloric acid, sulfuric acid, and nitric acid. Examples of solvents used in these reactions include water, THF, dioxane, and mixtures thereof. Reaction times are about 1 to 24 hours. In a preferred embodiment, compounds of formula (22) in THF are treated with 6M HCl, heated to reflux, and stirred for 6 hours to provide compounds of formula (20-c).

Scheme 8

(20)

(23)

As shown in Scheme 8, compounds of formula (20) can be converted to compounds of formula (23) by treatment with a formylating agent. Representative formylating agents include acetic anhydride/formic acid and 2,2,2-trifluoroethyl formate. Examples of solvents used in these reactions include formic acid, THF, MTBE, and mixtures thereof. The reaction temperature is about 25° C. to 65° C. and depends on the process chosen. Reaction times are typically 15 minutes to 6 hours.

Scheme 9

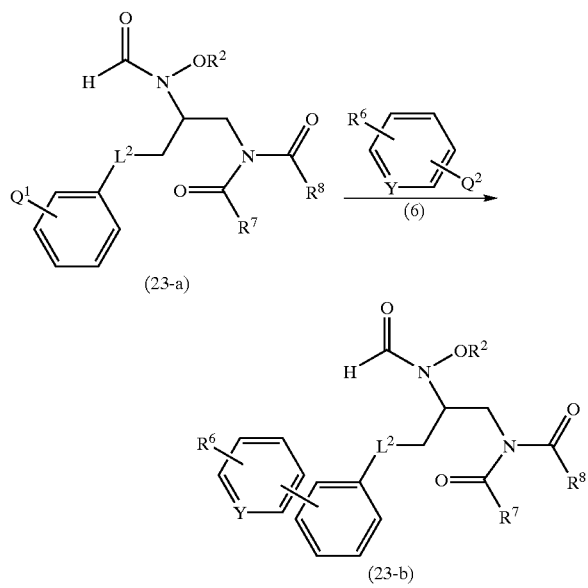

As shown in Scheme 9, compounds of formula (23-a), can be converted to compounds of (23-b) by the procedures described in Scheme 2.

Synthesis of (1S)-2-(4,4-dimethyl-2,5-dioxo-1-imidazolidinyl)-1-(((4'-(trifluoromethoxy)(1,1'-biphenyl)4-yl)oxy)methyl)ethyl(hydroxy)formamide

EXAMPLE 1A methyl (4S)-2-oxo-1,3-oxazolidine-4-carboxylate

A solution of L-serine methyl ester hydrochloride (3.063 kg) in dichloromethane (24.1 L) at 0° C. was treated with triethylamine (5.908 kg), stirred for 30 minutes, treated with triphosgene (1.949 kg) in dichloromethane (5.356 kg) over 6.5 hours, stirred for 45 minutes, treated with hexanes (12.23 kg), stirred for 55 minutes, and filtered with ethyl acetate (16.013 kg). The filtrate was concentrated to provide a 35% (w/w) solution of the desired product (93.5%, 98% ee) in ethyl acetate. $^1$H NMR (300 MHz, CDCl$_3$) δ6.55 (br s, 1H), 4.62 (dd, J=9, 9 Hz, 1H), 4.53 (dd, J=4, 9 Hz, 1H), 4.45 (dd, J=4, 9 Hz, 1H), 3.83 (s, 3H).

EXAMPLE 1B (4R)-4-(hydroxymethyl)-1,3-oxazolidin-2-one

The solution of Example 1A was concentrated to remove the bulk of the ethyl acetate, treated with ethanol (6.79 kg), concentrated to approximately one half of its original volume, treated again with ethanol (53.36 kg), cooled to 0° C., treated with sodium borohydride (855 g) over 3 hours and 42 minutes, stirred for 60 minutes, treated with phosphoric acid (2.20 kg) over 51 minutes, and warmed to room temperature over 18 hours to provide a reaction mixture with a pH of 5.55. The reaction mixture was filtered with ethanol (27.4 kg). The filtrate was concentrated to approximately 25 L and treated with toluene (30 L) to provide a white precipitate which was collected by filtration, rinsed with toluene (3 L), air dried, and vacuum dried (100 mmHg) at 45° C. with a nitrogen bleed to provide 3.592 kg (94.7%, >98% ee) of the desired product. $^1$H NMR (300 MHz, D$_2$O) δ4.36 (dd, J=9, 9 Hz, 1H), 4.20 (dd, J=6, 9 Hz, 1H), 3.90-3.80 (m, 1H), 3.48 (dd, J=3, 12 Hz, 1H), 3.40 (dd, J=4, 12 Hz, 1H).

EXAMPLE 1C ((4S)-2-oxo-1,3-oxazolidin-4-yl)methyl 4-methylbenzenesulfonate

A solution of Example 1B (3.430 kg) in pyridine (12.82 kg) at 5° C. was treated with para-toluenesulfonyl chloride (6.702 kg), stirred for 16 hours at room temperature, cooled to 5° C., treated with water (55.0 kg) over 1 hour and 48 minutes, warmed to room temperature, stirred for 17 hours, and filtered with water (28.2 kg). The filtrate was suction dried then vacuum dried (100 mmHg) at 50° C. with a nitrogen bleed to provide 6.895 kg (84.6%, >99% ee) of the desired product. $^1$H NMR (300 MHz, D$_2$O) δ7.9 (br s, 1H), 7.81 (d, J=9 Hz, 2H), 7.50 (d, J=9 Hz, 2H), 4.31 (t, J=9 Hz, 1H), 4.05-3.90 (m, 4H), 2.42 (s, 3H).

EXAMPLE 1D (4R)-4-((4-bromophenoxy)methyl)-1,3-oxazolidin-2-one

A solution of Example 1C (4.154 kg), potassium carbonate (2.522 kg), and 4-bromophenol (3.183 kg) in acetonitrile (30.3 kg) was stirred at 70° C. for 23.5 hours, cooled to 55° C., treated with 2% (w/w) K$_2$CO$_3$ (41.52 kg) over 20 minutes, cooled to room temperature, and separated into an aqueous fraction and an organic fraction. The organic fraction was concentrated to approximately one third of its original volume, treated with the aqueous fraction to provide a precipitate, concentrated to remove the remainder of the acetonitrile, treated with the 2% (w/w) K$_2$CO$_3$ solution (41.52 kg), stirred at room temperature for 18 hours, and filtered. The filter cake was rinsed with 2% K$_2$CO$_3$ (16.62 L) air-dried, slurried in ethyl acetate (9.44 kg), and heated at 55° C. This solution was treated with hexanes (23.615 kg) and cooled to room temperature to provide a solid. The solid was filtered, rinsed with a solution of ethyl acetate (2.24 kg) and hexanes (7.3 kg), air dried, and vacuum dried (100 mnu/Hg) at 50° C. with a nitrogen bleed to provide 3.307 kg (79.6%, >99.5% ee) of the desired compound. $^1$H NMR (300 MHz, DMSO-d$_6$) δ7.91 (br s, 1H), 7.47 (dd, J=17 Hz, 2H), 6.93 (dd, J=17 Hz, 2H), 4.44 (m, 1H), 4.15 (m, 2H), 3.95 (m, 2H).

EXAMPLE 1E 4-(trifluoromethoxy)phenylboronic acid

A solution of 1-bromo-4-(trifluoromethoxy)benzene (1.69 kg) and triisopropyl borate (1.46 kg) in THF (6.75 L) at −70° C. was treated with 2.25 M butyllithium in hexanes (3.27 L) over 2.3 hours, stirred for 10 minutes, treated with 6M HCl (1.52 L) over 50 minutes, stirred for 18 hours at room temperature, and poured into a mixture of heptane (8.43 L) and 20% (w/w) sodium chloride (8.44 kg). This mixture was stirred for 10 minutes and separated into an aqueous fraction and an organic fraction. The organic fraction was concentrated to provide a white paste. The paste was dried under vacuum (100 mmHg) at ambient temperature with a nitrogen bleed for 2 days then at 40–50° C. for 18 hours to provide 1.306 kg (90.4%) of the desired product as a solid. $^1$H NMR (CDCl$_3$, 300 MHz) δ7.24-7.19 (m, 2H), 8.14-8.10 (m, 2H)

with additional absorptions at 7.19-7.15 (m, 2H) and 8.04-8.00 (m, 2H) corresponding to the cyclic boronic acid trimer.

EXAMPLE 1F (4R)-4-(((4'-(trifluoromethoxy)(1,1'-biphenyl)-4-yl)oxy)methyl)-1,3-oxazolidin-2-one A room temperature solution of potassium phosphate (9.22 kg, 43.4 mol) in water (25 L) was treated sequentially with Example 1D (3.94 kg), a solution of Example 1E (3.15 kg) in THF (19.6 L), and THF (5.1 L), sparged with nitrogen for 20 minutes, treated with Pd(dppf)Cl$_2$ (59.4 g), purged with nitrogen, heated to 60–65° C. for 1 hour, cooled to ambient temperature, concentrated, and treated with water (25 L). The resulting mixture was repeatedly filtered until the filtrate was clear, and the solid was washed with water (4×25 L) until the pH of the wash was neutral. The solid was dried, treated with THF (51.1 L), concentrated, treated with THF (37.1 L), concentrated again, and treated with THF (68.1 L). Commercial Deloxan resin (3.2 kg) was dehydrated by rinsing with methanol (4× 4 L) and THF (16.1 L), added to the solution of product in THF, and stirred at ambient temperature for 18 hours. The mixture was filtered through a pad of silica gel 60 (10.3 kg slurried with THF) and the pad was thoroughly rinsed with THF. The combined filtrates were concentrated to a volume of approximately 11 L, treated with heptanes (59.7 L), stirred for 1 hour and filtered. The solid was washed with heptanes (2×14.6 L) and dried at 45° C. under vacuum for 18 hours to provide 4.93 kg (97%, >99% ee) of the desired product. MS (DCI/NH$_3$) m/z 371 (M+NH$_4$)$^+$; $^1$H NMR (300 MHz, DMSO-d$_6$) δ7.96 (br s, 1H), 7.73 (d, J=8.8 Hz, 2H), 7.62 (d, J=8.8 Hz, 2H), 7.40 (d, J=8.8 Hz, 2H), 7.05 (d, J=8.8 Hz, 2H), 4.46 (t, J=10.0 Hz, 1H), 4.18 (m, 2H), 4.06 (dd, J=10.0 Hz, 4.1 Hz, 1H), 3.99 (dd, J=10.0 Hz, 5.0 Hz, 1H); $^{13}$C NMR (DMSO-d$_6$) d 158.9 (q), 158.3 (q), 147.4 (q), 139.1 (q), 131.6 (q), 128.0 (CH), 121.5 (CH), 115.2 (CH), 69.4 (CH$_2$), 66.2 (CH$_2$), 51.0 (CH).

EXAMPLE 1G (2 S)-2-amino-3-((4'-(trifluoromethoxy)(1,1'-biphenyl)-4-yl)oxy)-1-propanol A solution of KOH (2.502 kg) in water (2.492 kg) at 0° C. was treated sequentially with ethanol (11.548 kg) and Example 1F, stirred at 80° C. for 7 hours, treated with water (37.059 kg) over 25 minutes, and cooled to room temperature over 18 hours to provide a solid. The solid was filtered, washed with water (7.035 kg), and dried under vacuum (100 mm Hg) at 50° C. with a nitrogen bleed to provide 3.316 kg (96.6%, >99.5% ee) of the desired product. $^1$H NMR (300 MHz, DMSO-d$_6$) δ7.83 (dt, J=3.9 Hz, 2H), 7.71 (dt, J=3, 9 Hz, 2H), 7.52 (d, J=9 Hz, 2H), 7.14 (dt, J=3, 9 Hz, 2H), 4.77 (br s, 1H), 4.01 (m, 2H), 3.51 (m, 2H), 3.15 (t, J=5 Hz 1H).

EXAMPLE 1H (2S)-2-(((E)-(4-methoxyphenyl)methylidene)amino)-3-((4'-(trifluoromethoxy)(1,1'-biphenyl)-4-yl)oxy)-1-propanol A solution of Example 1G (3.236 kg) and para-anisaldehyde (1.484 kg) in toluene (6.631 kg) was heated at 80° C. for 2 hours, treated with heptane (33.147 kg) over 50 minutes, cooled to room temperature over 20 hours, and filtered. The filter cake was rinsed with heptane (6.994 kg), air dried, then vacuum dried (100 mmHg) at 50° C. to provide 4.297 kg (97.6%) of the desired product. $^1$H NMR (300 MHz, DMSO-d$_6$) δ8.35 (s, 1H), 7.73 (dt, 2H, J=8.9, 2.9 Hz), 7.61 (dt, 2H, J=8.8, 2.9 Hz), 7.41 (dd, 2H, J=8.9, 1.1 Hz), 7.05 (dt, 2H, J=8.8, 2.9 Hz), 7.01 (dt, 2H, J=8.8, 2.9 Hz), 4.87 (br s, 1H), 4.31 (dd, 1H, J=9.9, 4.1 Hz), 4.13 (dd, 1H, J=9.9, 7.4 Hz), 3.81 (s, 3H), 3.64–3.80 (m, 2H), 3.56 (dd, 1H, J=10.0, 6.3 Hz).

EXAMPLE 1I 3-((2S)-2-(((E)-(4-methoxyphenyl)methylidene)amino)-3-((4'-(trifluoromethoxy)(1,1'-biphenyl)-4-yl)oxy)propyl)-5,5-dimethyl-2,4-imidazolidinedione A solution of Example 1H (2.80 kg), triphenylphosphine (2.475 kg), and 5,5-dimethylhydantoin (1.37 kg) in THF (24.89 kg) at 1–2° C. was treated with diisopropyl azodicarboxylate (2.01 kg) over 75 minutes to provide a solution of the desired product.

EXAMPLE 1J 3-((2S)-2-(3-(4-methoxyphenyl)-1,2-oxaziridin-2-yl)-3-((4-(trifluoromethoxy)(1,1'-biphenyl)-4-yl)oxy)propyl)-5,5-dimethyl-2,4-imidazolidinedione The solution of Step 1I was cooled to –67° C., treated with a solution of 3-chloroperoxybenzoic acid (3.15 kg) in THF (6.30 kg) over 30 minutes, and warmed to 0–2° C. over 100 minutes to provide a solution of the desired product.

EXAMPLE 1K 3-((2S)-2-(hydroxyamino)-3-((4'-(trifluoromethoxy)(1,1'-biphenyl)-4-yl)oxy)propyl)-5,5-dimethyl-2,4-imidazolidinedione, para toluene sulfononic acid salt The solution of Example 1J was diluted with toluene (27.34 kg) and washed sequentially with 10% (w/w) sodium thiosulfate (31 kg), 5% (w/w) sodium bicarbonate (31 kg), and 10% (w/w) sodium chloride (30 kg). The mixture was treated with para-toluenesulfonic acid hydrate (1.79 kg), stirred at ambient temperature several hours, treated with a solution of N-hydroxylamine hydrochloride (0.88 kg) in water (2.8 kg), and stirred at ambient temperature several hours. The reaction mixture was washed with 10% (w/w) sodium carbonate (31 kg) and 5% (w/w) sodium bicarbonate (30 kg), diluted with ethyl acetate (9.47 kg), washed with 10% (w/w) sodium chloride (30 kg), concentrated, and diluted to a concentration of 30 mg/mL in toluene. The solution was treated with para-toluenesulfonic acid hydrate (19.5 g), stirred for 2 hours, filtered through a pad of diatomaceous earth (Celite® 521), treated with para-toluenesulfonic acid hydrate (1.05 kg), and warmed to 50° C. to provide a white suspension which thickened after 30 minutes. After six hours the heating was discontinued, the suspension was cooled to ambient temperature, stirred for 18 hours, and filtered. The filter cake was rinsed with toluene (29 kg), suction dried, then vacuum dried (100 mm Hg) at 40–45° C. with a nitrogen bleed to provide 3.422 kg (83% potency adjusted yield) of the desired product. $^1$H NMR (300 MHz, DMSO-d$_6$) δ11.4 (br s, 1H), 10.8 (br s, 1H), 8.48 (s, 1H), 7.66 (dt, 2H, J=8.8, 2.9 Hz), 7.68 (dt, 2H, J=8.8, 2.9 Hz), 7.50 (dt, 2H, J=8.0, 1.4 Hz), 7.45 (d, 2H, J=8.0 Hz), 7.13 (d, 2H, J=8.0 Hz), 7.08 (dt, 2H, J=8.0, 1.4 Hz), 4.30 (dd, 1H, J=3.6, 11.0 Hz), 4.21 (dd, 1H, J=4.4, 11.0 Hz), 4.0-3.9 (m, 1H), 3.90-3.75 (m, 2H), 2.30 (s, 3H), 1.31 (br s, 6H). The NMR spectrum also showed approximately 5 wt % toluene.

EXAMPLE 1L

2,2,2-trifluoroethyl formate

A solution of 2,2,2-trifluoroethanol (18.212 kg) and formic acid (36.324 kg) was stirred at 80° C. for 6 hours, cooled to room temperature, and stirred for 18 hours to provide a mixture of product and unreacted starting materials. The mixture was distilled (head temperature 60–80° C.) over 23 hours to provide a distillate (14.79 kg) comprising 10.64 kg (71.9% (w/w) solution, 45.5%) of the desired product in addition to unreacted starting materials. $^1$H NMR (300 MHz, CDCl$_3$) (71.9:13.6:4.4/2,2,2-trifluoroethyl formate:2,2,2-trifluoroethanol:formic acid): formic acid: δ8.06 (s, 1H); 2,2,2-trifluoroethanol: δ3.96 (q, 2H, J=8.8 Hz); and 2,2,2-trifluoroethyl formate: δ8.13 (q, 1H, J=0.7 Hz), 4.57 (dq, 2H, J=0.7, 8.4 Hz).

EXAMPLE 1M

3-((2S)-2-(hydroxyamino)-3-((4'-(trifluoromethoxy)(1,1'-biphenyl)-4-yl)oxy)propyl)-5,5-dimethyl-2,4-imidazolidinedione A solution of the product from Example 1K (1.95 kg) in 15% (w/w) potassium carbonate (4.29 kg), THF (5.07 kg), and methyl tert-butyl ether (4.12 kg) was stirred until all solids dissolved and separated into an aqueous fraction and an organic fraction. The organic fraction was washed with 25% (w/w) sodium chloride (3.83 kg), treated with THF (0.58 kg), and concentrated to provide a 20–30% (w/w) solution of the desired product.

EXAMPLE 1N

(1 S)-2-(4,4-dimethyl-2,5-dioxo-1-imidazolidinyl)-1-(((4'-(trifluoromethoxy)(1,1'biphenyl)-4-yl)oxy)methyl)ethyl(hydroxy)formamide The solution of Example 1M was treated with the distillate containing Example 1L (5.27 kg of the 71.9% (w/w) solution (3.79 kg, 10 equivalents), stirred at reflux for 4 hours, cooled to less than 30° C., treated with water (5.33 kg) and MTBE (7.62 kg), washed with 15% (w/w) potassium bicarbonate (5.3 kg portions) until the pH of the wash was ≧8, and concentrated. The residue was dissolved in ethyl acetate (7.133 kg), treated with heptane (10.71 kg) during which a solid began to precipitate, stirred for 18 hours, and filtered. The filter cake was rinsed with 1:2 (v/v) ethyl acatate/heptane (5.63 kg), suction dried, then vacuum dried (100 mmHg) at 100° C. with a nitrogen bleed to provide 2.685 kg (91.8%, ≧99% ee) of the desired product. $^1$H NMR (300 MHz, DMSO-d$_6$) δ9.95 (br s, 0.5H), 9.80 (br s, 0.5H), 8.41 (br s, 0.5H), 8.37 (br s, 0.5H), 8.35 (s, 0.5H), 7.95 (s, 0.5H), 7.76 (d, 2H, J=8.9 Hz), 7.65 (d, 2H, J=8.5 Hz), 7.43 (d, 2H, J=8.5 Hz), 7.04 (d, 2H, J=8.9 Hz), 4.92-4.80 (m, 0.5H), 4.50-4.38 (m, 0.5H), 4.28-4.06 (m, 2H), 3.82-3.68 (m, 1H), 3.66-3.54 (m, 1H), 3.88 (s, 3H), 3.84 (s, 3H).

ALTERNATE SYNTHESIS OF EXAMPLE 1M

EXAMPLE 2A

(2S)-2-amino-3-(4-bromophenoxy)-1-propanol

The desired product (160 g) was prepared by substituting Example 1D (177 g) for Example 1F in Example 1G. $^1$H NMR (300 MHz, DMSO-d$_6$) δ7.38 (d, 2H, J=7.2 Hz), 6.85 (d, 2H, J=7.2 Hz), 3.79 (m,2H), 3.35 (m, 2H), 2.95 (m, 1H).

EXAMPLE 2B

(2S)-3-(4-bromophenoxy)-2-(((E)-(4-methoxyphenyl)methylidene)amino)-1-propanol The desired product (225 g) was prepared by substituting Example 2A (155 g) for Example 1G in Example 1H. $^1$H NMR (300 MHz, DMSO-d$_6$) δ8.3 (s, 1H), 7.69 (d, 2H, J=9 Hz), 7.41 (d, 2H, J=9 Hz), 6.99 (d, 2H, J=9 Hz), 6.90 (d, 2H, J=9 Hz), 4.81 (m, 1H), 4.15 (m, 2H), 3.80 (s, 3H), 3.61 (m, 3H).

EXAMPLE 2C

3-((2S)-3-(4-bromophenoxy)-2-(((E)-(4-methoxyphenyl)methylidene)anino)propyl)-5,5-dimethyl-2,4-imidazolidinedione The desired product was prepared without isolation by substituting Example 2B (208 g) for Example 1H in Example 1H.

EXAMPLE 2D

3-((2S)-3-(4-bromophenoxy)-2-(3-(4-methoxyphenyl)-1,2-oxaziridin-2-yl)propyl)-5,5-dimethyl-2,4-imidazolidinedione The desired product was prepared without isolation by substituting the in situ derived Example 2C for Example 1I in Example 1J.

EXAMPLE 2E

3-((2S)-3-(4-bromophenoxy)-2-(hydroxyamino)propyl)-5,5-dimethyl-2,4-imidazolidinedione The desired product (113 g) was prepared by substituting in situ prepared Example 2D for Example 1J in Example 1K. $^1$H NMR (300 MHz, DMSO-d$_6$) δ8.22 (br S, 1H), 7.35 (m, 2H), 7.22 (br s, 1H), 6.80 (m, 2H), 5.74 (br s, 1H), 3.85 (m, 2H), 3.47 (m, 2H), 3.25 (m, 1H), 1.19 (s, 3H), 1.17 (s, 3H).

EXAMPLE 1M

3-((2S)-2-(hydroxyamino)-3-((4'-(trifluoromethoxy)(1,1'-biphenyl)-4-yl)oxy)propyl)-5,5-dimethyl-2,4-imidazolidinedione The desired product (94 g) was prepared by substituting Example 2E (108 g) for Example 1D in Example 1F. $^1$H NMR (300 MHz, DMSO-d$_6$) δ8.21 (br s, 1H), 7.55 (m, 2H), 7.44 (m, 2H), 7.21 (m, 2H), 7.12 (br s, 1H), 6.80 (m, 2H), 5.64 (br s, 1H), 3.89 (m, 1H), 3.75 (m, 1H), 3.39 (m, 2H), 3.13 (m, 1H), 1.08 (s, 3H), 1.06 (s, 3H).

Synthesis of (1R)-2-(4,4-dimethyl-2,5-dioxo-1-imidazolidinyl)-1-(((4'-(trifluoromethoxy)(1,1'-biphenyl)4-yl)oxy)methyl)ethyl(hydroxy)formamide

EXAMPLE 3A ethyl 4-(4-bromophenoxy)-3-oxobutanoate

A solution of 50% (w/w) NaOH in water (188 mL) in DMSO (800 mL) was stirred at room temperature until a precipitate formed, treated dropwise with a solution of 4-bromophenol (101.2 g) in DMSO (200 mL) over 25 minutes, stirred for 25 minutes, treated with ethyl 4-chloro-3-oxobutanoate (102.2 g) over 40 minutes, adjusted to pH 3 with 6M HCl, treated with water (200 mL) over 12 minutes, stirred for 5 hours, treated with water (150 mL) over 20 minutes, and filtered. The solid was washed with sequentially with water and 40% ethanol/water and dried under vacuum (100 mm Hg) at 50° C. with a nitrogen bleed to provide 119.8 g of the desired product. $^1$H NMR (300 MHz, CDCl$_3$) δ7.40 (m, 2H), 6.79 (m, 2H), 4.65 (s, 2H), 4.20 (q, 2H, J=7 Hz), 3.62 (s, 2H), 1.26 (t, 3H, J=7Hz).

EXAMPLE 3B ethyl 4-(4-bromophenoxy)-3-hydroxybutanoate

A solution of Example 3A (99.5 g) in ethanol (480 mL) was deoxygenated with nitrogen, treated with (Ru$_2$Cl$_5$(R)-BINAP$_2$)$^-$Et$_2$NH$_2$$^+$ (825 mg) and 2M HCl (0.5 mL), flushed with nitrogen, heated to 100° C. with shaking under 50 psi of hydrogen for 8 hours, cooled, treated with hexanes (30 mL), and filtered to provide a solution of the desired product. $^1$H NMR (300 MHz, CDCl$_3$) δ7.37 (m, 2H), 6.80 (m, 2H), 4.41 (m, 1H), 4.20 (q, 2H, J=7 Hz), 3.96 (d, 2H, J=6Hz), 3.19 (d, 1H, J=6 Hz), 2.67 (m, 2H), 1.30 (t, 3H, J=7 Hz).

EXAMPLE 3C (3S)-4-(4-bromophenoxy)-3-hydroxybutanoic acid

The solution of Example 3B (154.2 g) was cooled to 5° C. treated with 44% (w/w) KOH over 10 minutes, warmed to room temperature, treated with water (150 mL), concentrated, treated with isopropyl acetate (500 mL) and water (200 mL), cooled to 5° C., adjusted to pH 2 with 6M HCl, and treated with additional isopropyl acetate (500 mL). The aqueous phase was extracted with isopropyl acetate (100 mL). The extract was washed with brine, dried (Na$_2$SO$_4$), filtered, concentrated to a volume of 310 mL, and treated with isopropyl acetate (70 mL) and heptane (1.2 L) dropwise over 4 hours to provide a precipitate. The precipitate was collected by filtration, washed with 20% isopropyl acetate in heptane (700 mL), and dried under vacuum (100 mm Hg) at 50° C. with a nitrogen bleed to provide 121.3 g of the desired product. $^1$H NMR (300 MHz, DMSO-d$_6$) δ7.50 (m, 2H), 6.96 (m, 2H), 5.3 (br s, 1H), 4.23, (m, 1H), 3.95 (d, 2H, J=6 Hz), 2.60 (dd, 1H, J=6, 15 Hz), 2.43 (dd, 1H, J=8, 15 Hz).

EXAMPLE 3D (3 S)-N-(benzyloxy)-4-(4-bromophenoxy)-3-hydroxybutanamide

A solution of Example 3C (121.2 g) in DMF (1 L) at 5° C. was treated sequentially with 1-[3-(dimethylamino) propyl]-3-ethylcarbodiimide methiodide (92.9 g), 1-hydroxybenzotriazole (68.5 g), and 4-methylmorpholine (193 mL), stirred for 5 minutes, treated with O-benzylhydroxylamine hydrochloride (73.5 g), warmed to room temperature, treated with 5% HCl (2.1 L) over 35 minutes, and filtered. The solid was washed with water and dried under vacuum (100 mm Hg) at 50° C. with a nitrogen bleed to provide 156.9 g of the desired product. $^1$H NMR (300 MHz, DMSO-d$_6$) δ11.05 (s, 1H), 7.45 (m, 2H), 7.35 (m, 5H), 6.90 (m, 2H), 5.21 (d, 1H, J=5 Hz), 4.80 (s, 2H), 4.20 (m, 1H), 3.88 (m, 2H), 2.25 (dd, 1H, 6, 14 Hz), 2.15 (dd, 1H, J=8,14 Hz).

EXAMPLE 3E (3R)-3-((benzyloxy)amino)-4-(4-bromophenoxy) butanoic acid lithium salt A solution of triphenylphosphine (121 g) in THF (1.9 L) was treated with DEAD (80.1 g) over 30 minutes, treated with a solution of Example 3D in DMF (600 mL) at 40° C. by cannula over 90 minutes and a solution of triphenylphosphine (6.2 g) and DEAD (3.8 mL) in THF (20 mL), concentrated, treated with toluene (350 mL), and concentrated. The concentrate was treated with toluene (1.9 L), washed with water, and concentrated to half of its original volume, to provide a solution of (4R)-1-(benzyloxy)-4-((4-bromophenoxy)-methyl)-2-azetidinone. $^1$H NMR (300 MHz, CDCl$_3$) δ7.4 (m, 7H), 6.70 (m, 2H), 5.00 (d, 1H, J=10), 4.92 (d, 1H, J=12 Hz), 3.86 (m, 1H), 3.82 (dd, 1H, J=1, 4 Hz), 2.81 (dd, 1H, J=6, 15 Hz), 2.66 (dd, 1H, J=2, 15 Hz).

This solution was treated with a solution of LiOH (27.3 g) in water (240 mL), heated to 60° C. for 3 hours, cooled to room temperature, stirred for 16 hours, treated with a solution of lithium hydroxide (12.3 g) in water (120 mL), heated to 65° C. for 16 hours, cooled to room temperature, stirred for 2 hours, and filtered. The precipitate was washed with toluene (200 mL), and the filtrate was concentrated to half the original volume, treated with a small amount of the collected solid, and stirred at room temperature for 16 hours. The resulting precipitate was collected by filtration, and the combined solids were treated with toluene (920 mL), heated to 95° C., cooled to room temperature, and stirred for 16 hours. The resulting precipitate was collected by filtration, then dried under vacuum (100 mm Hg) at 50° C. with a nitrogen bleed to provide 87.1 g of the desired product. $^1$H NMR (300 MHz, DMSO-d$_6$) δ7.43 (m, 2H), 7.30 (m, 5H), 6.91 (m, 2H), 4.60 (dd, 2H, J=2, 12 Hz) 3.96 (dd, 1H, J=4, 10 Hz), 3.85 (dd, 1H, J=6, 10 Hz), 2.13 (dd, 1H, J=5, 16 Hz), 1.99 (dd, 1H, J=8, 16 Hz).

EXAMPLE 3F (5R)-1-(benzyloxy)-5-((4-bromophenoxy)methyl)-2-imidazolidinone

A suspension of Example 3E in THF (2.1 L) was treated with DPPA (90.5 g) and diisopropylethyl amine (56 mL), heated to reflux, stirred for 3 hours, cooled to 30° C., poured into ice cold 10% HCl, and stirred vigorously. The organic phase was treated with 10% HCl (500 mL) and NaCl (75 g). The aqueous phase was separated and washed with ethyl acetate. The extract was washed sequentially with water, saturated NaHCO$_3$, and brine and concentrated. The concentrate was treated with toluene (550 mL), warmed to reflux, cooled to 35° C., treated with heptane (800 mL) over 2 hours, and filtered. The solid was dissolved in 1:1 THF/toluene (700 mL), and the resulting solution was washed with saturated NaHCO$_3$ and brine, and concentrated. The solid was dried under vacuum (100 mm Hg) at 50° C. with a nitrogen bleed to provide 54.6 g of the desired product. $^1$H NMR (300 MHz, CDCl$_3$) δ7.45 (m, 2H) 7.35 (m, 5H), 6.58 (m, 2H), 5.35 (br s, 1H), 5.05 (d, 1H, J=11 Hz), 4.94 (d, 1H, J=11 Hz), 3.85 (m, 1H), 3.73 (dd, 1H, J=7, 9 Hz), 3.55 (dd, 1H, J=7, 9 Hz), 3.51 (t, 1H, J=8 Hz), 3.25 (t, 1H, J=9 Hz).

EXAMPLE 3G (2R)-2-((benzyloxy)amino)-3-(4-bromophenoxy)-1-propanamine

A mixture of Example 3F in ethanol (300 mL) was treated with a solution of 30% (w/w) KOH in water (100 mL), heated to reflux, stirred for 8 hours, treated with additional 30% KOH in water (5 mL), stirred for 40 minutes, cooled to room temperature, concentrated to a slurry, and extracted with toluene. The extract was washed with 1M NaOH and brine, dried (Na$_2$SO$_4$), filtered, and concentrated to provide 48.6 g of the desired product. $^1$H NMR (300 MHz, DMSO-d$_6$) δ7.45 (m, 2H), 7.33 (m, 5H), 6.90 (m, 2H), 6.67 (d, 1H, J=5 Hz), 4.63 (s, 2H), 3.95 (m, 2H), 3.08 (m, 1H), 2.73 (m, 1H), 2.62 (m, 1H), 1.40 (br s, 2H).

EXAMPLE 3H 3-((2R)-2-((benzyloxy)amino)-3-(4-bromophenoxy) propyl)-5,5-dimethyl-2,4-imidazolidinedione A solution of 2-aminoisobutyric acid (51.7 g) in methanol (500 mL) at 0° C. was treated with thionyl chloride (80.4 g) over 35 minutes, stirred for 30 minutes, warmed to room temperature, heated to 50° C. for 3 hours, cooled to room temperature, and concentrated. The concentrate was dissolved in methanol (200 mL), concentrated, dissolved in warm methanol (50 mL), treated with diethyl ether (300 mL), and filtered. The resulting solid was dried under vacuum (100 mm Hg) at 50° C. with a nitrogen bleed to provide 59.6 g of methyl 2-amino-2-methylpropanoate hydrochloride.

A solution of the methyl 2-amino-2-methylpropanoate hydrochloride(65.5 g) in THF (650 mL) was treated with triethylamine (60 mL), heated to reflux, stirred for 30 minutes, cooled to room temperature, treated dropwise with a solution of triphosgene (43.2 g) in THF (250 mL) over 5 minutes, heated to reflux, stirred for 4 hours, cooled to 15° C., treated with triethylamine (120 mL) over 7 minutes, heated to reflux, stirred for 40 minutes, cooled to room temperature, and filtered. The solid was washed with THF and the filtrate was collected to provide a solution of methyl 2-isocyanato-2-methylpropanoate in THF.

A solution of Example 3G (19.7 g) in THF (100 mL) at room temperature was treated with the solution of the methyl 2-isocyanato-2-methylpropanoate in THF, stirred for 25 minutes, and concentrated to a volume of 170 mL. The concentrate was treated with THF (80 mL) and 6M HCl (95 mL), heated to reflux, stirred for 6 hours, cooled to room temperature, concentrated, and extracted with isopropyl acetate. The extract was washed sequentially with water, saturated NaHCO$_3$, and brine, dried (Na$_2$SO$_4$), filtered, and concentrated to provide 24.2 g of the desired product. $^1$H NMR (300 MHz, DMSO-d$_6$) δ8.33 (s, 1H), 7.47 (m, 2H), 7.35 (m, 5H), 6.90 (m, 2H), 6.78 (d, 1H, J=5 Hz), 4.65 (m, 2H), 4.00 (m, 2H), 3.68 (m, 1H), 3.55 (m, 2H), 1.30 (s, 3H), 1.28 (s, 3H).

EXAMPLE 3I benzyloxy((1R)-2-(4-bromophenoxy)-1-((4,4-dimethyl-2,5-dioxo-1-imidazolidinyl)methyl)ethyl) formamide A solution of Example 3H (57.7 g) in formic acid (200 mL) was treated with a mixture of acetic anhydride (35 mL) in formic acid (35 mL) over 10 minutes, stirred for 10 minutes, and concentrated. The concentrate was dissolved in ethyl acetate (500 mL), washed sequentially with 1:1/water:brine, saturated NaHCO$_3$, and brine, dried (Na$_2$SO$_4$), filtered, and concentrated. The concentrate was dissolved in warm (60° C.) toluene, cooled, and filtered. The solid was washed with 1:1/toluene:heptane then dried under vacuum (100 mm Hg) at 50° C. with a nitrogen bleed to provide 51.7 g of the desired product. $^1$H NMR (300 MHz, DMSO-d$_6$) δ8.42 (br s, 0.5H), 8.38 (br s, 0.5H), 8.32 (br s, 0.5H), 8.10 (br s, 0.5H), 7.4 (m, 7H), 6.95 (m, 2H), 5.00 (m, 1H), 4.91 (m, 1H) 4.80 (m, 0.5H), 4.55 (m, 0.5H), 4.28(m, 1H), 4.17 (m, 1H), 3.88 (dd, 1H, J=9, 14 Hz), 3.60 (m, 1H), 1.25 (s, 3H), 1.22 (s, 3H).

EXAMPLE 3J 4-(((2R)-2-((benzyloxy)(formyl)amino)-3-(4,4-dimethyl-2,5-dioxo-1-imidazolidinyl)propyl)oxy)-4'-(trifluoromethoxy)-1,1'-biphenyl A mixture of magnesium (3.25 g) in THF (25 mL) at room temperature was treated with several drops of 1-bromo-4-(trifluoromethoxy)benzene, stirred for several minutes, treated with THF (100 mL), treated with 1-bromo-4-(trifluoromethoxy)benzene (30.8 g), heated to reflux, stirred for 16 hours, treated with triisopropyl borate (34 mL) over 10 minutes, stirred for 1 hour, cooled to 0° C., treated with 6M HCl (50 mL), stirred for 45 minutes, and extracted with isopropyl acetate. The extract was washed with brine, filtered, and concentrated to provide 21.5 g of 4-(trifluoromethoxy)phenylboronic acid.

A solution of 2M Na$_2$CO$_3$ (180 mL) in toluene (180 mL) was sparged with nitrogen, treated with Example 3I (49.8 g), 4-(trifluoromethoxy)phenylboronic acid (21.5 g), and Pd(PPh$_3$)$_4$ (0.68 g), heated to reflux, stirred for 1 hour, treated with additional boronic acid (6.4 g), refluxed for 2 hours, and cooled to room temperature. The organic phase was washed with brine, dried (Na$_2$SO$_4$), filtered, and concentrated. The concentrate was purified on a flash silica gel plug with 4:1/hexanes:ethyl acetate to 1:3/hexanes:ethyl acetate to provide 49.6 g of the desired product. $^1$H NMR (300 MHz, DMSO-d$_6$) δ8.25 (br s, 1H), 8.07 (br s, 1H), 7.75 (m, 2H), 7.61 (m, 2H), 7.40 (m, 7H), 7.05 (m, 2H), 5.04 (d, 1H, J=10 Hz), 4.98 (d, 1H, J=10 Hz), 4.70 (br s, 1H), 4.33 (dd, 1H, J=8, 10 Hz), 4.26 (dd, 1H, J=5, 10 Hz), 3.90 (dd, 1H, J=8, 14 Hz), 3.67 (dd, 1H, J=5, 14 Hz), 1.26(s, 3H).

EXAMPLE 3K (1R)-2-(4,4-dimethyl-2,5-dioxo-1-imidazolidinyl)-1-(((4'-(trifluoromethoxy)(1,1'-biphenyl)-4-yl)oxy) methyl)ethyl(hydroxy)formamide A solution of Example 3J (65.9 g) in ethyl acetate (450 mL) was treated with 10% Pd/C (10 g), and shaken under a hydrogen atmosphere (50 psi) at room temperature for 8 hours, filtered through a 0.45 μm nylon millipore filter, concentrated, treated with toluene, concentrated, dissolved in warm (75° C.) toluene, cooled to 60° C., and filtered. The filtrate was cooled to room temperature, treated with heptane (100 mL) over 45 minutes, stirred for 72 hours, and filtered. The solid was washed with heptane and dried under vacuum (100 mm Hg) at 50° C. with a nitrogen bleed to provide 39.7 g of the desired product.

What is claimed is:

1. A process for preparing a compound of formula (5-a)

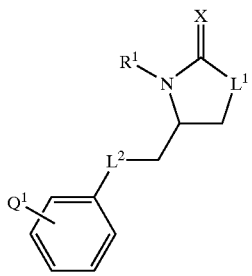

(5-a)

wherein
X is O or S;
R¹ is selected from the group consiting of hydrogen, an amino protecting group, and —OR²;
R² is hydrogen protecting group;
L¹ is —O— or —N(R³)—, wherein R³ is hydrogen or an amino protecting group;
L² is —O— or —S—; and
Q¹ is selected from the group consisting of halide, methanesulfonate, and trifluoromethanesulfonate;
the process comprising:
(a) activating the hydroxyl of the compound of formula (3)

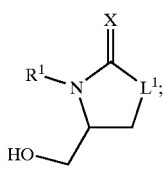

(3)

wherein X, R¹ and L¹ are as defined above,
(b) reacting the product of step (a), a compound of formula (4)

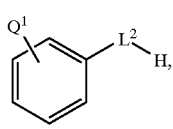

(4)

wherein L² and Q¹ are as defined above, and base to provide the compound of formula (5-a)

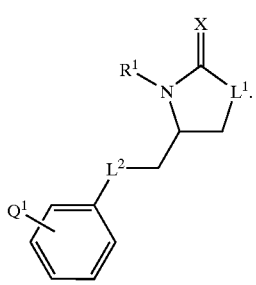

(5-a)

2. The process of claim 1, wherein the compound of formula (5-a) is (4R)-4-((4-bromophenoxy)methyl)-1,3-oxazolidin-2-one.

3. A process for preparing a compound of formula (5-b)

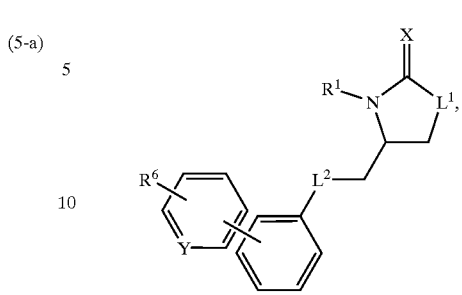

(5-b)

wherein
X is O or S;
R¹ is selected from the group consisting of hydrogen, an amino protecting group, and —OR²;
R² is hydrogen or a hydroxy protecting group;
L¹ is —O— or —N(R³)—, wherein R³ is hydrogen or an amino protecting group;
L² is —O— or —S—;
Y is C(H);
R⁶ is selected from the group consisting of alkoxy, alkoxyalkyl, alkyl, aminosulfonyl, aminosulfonylalkyl, aryl, arylalkyl, cyano, cyanoalkyl, halo, haloalkyl, (heterocycle)oxy, (heterocycle)oxyalkyl, hydroxy, hydroxyalkyl, phenylalkoxy, phenylalkoxyalkyl phenoxy, phenoxyalkyl, perfluoroalkoxy, perfluoroalkoxyalkyl, perfluorothioalkoxy, perfluorothioalkoxyalkyl, sulfinyl, sulfinylalkylsulfonyl, sulfonylalkyl, thioalkoxy, and thioalkoxyalkyl;
the process comprising:
reacting a compound of formula (5-a)

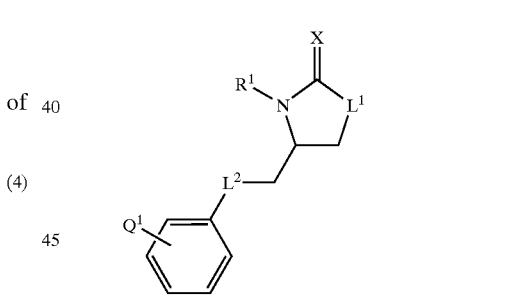

(5-a)

wherein X, R¹, L¹, L² and Q¹ are as defined above, and a compound of formula (6)

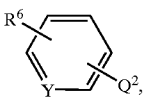

(6)

wherein
R⁶ and Y are as defined above; and
Q² is selected from the group consisting of trialkylstannanes, boronic acid, boronic esters, magnesium halides, zinc halides, and silyl(alkyl) cyclobutanes,
and a coupling catalyst.

4. The process of claim 3, wherein the compound of formula (5-b) is (4R)-4-((4'-(trifluoromethoxy)(1,1'-biphenyl)-4-yl)oxy)methyl)-1,3-oxazolidin-2one.

* * * * *